(12) United States Patent
Okada

(10) Patent No.: US 7,396,898 B2
(45) Date of Patent: Jul. 8, 2008

(54) DIAMINE, ACID DIANHYDRIDE, AND REACTIVE GROUP CONTAINING POLYIMIDE COMPOSITION PREPARED THEREFROM AND PROCESS OF PREPARING THEM

(75) Inventor: Koji Okada, Osaka (JP)

(73) Assignee: Kaneka Corporation, Osaka (JP)

( * ) Notice: Subject to any disclaimer, the term of this patent is extended or adjusted under 35 U.S.C. 154(b) by 427 days.

(21) Appl. No.: 10/474,855

(22) PCT Filed: Apr. 12, 2002

(86) PCT No.: PCT/JP02/03710

§ 371 (c)(1),
(2), (4) Date: Oct. 9, 2003

(87) PCT Pub. No.: WO02/083659

PCT Pub. Date: Oct. 24, 2002

(65) Prior Publication Data

US 2004/0158030 A1    Aug. 12, 2004

(30) Foreign Application Priority Data

Apr. 13, 2001  (JP)  ............................. 2001-116220
Apr. 13, 2001  (JP)  ............................. 2001-116221
May 31, 2001  (JP)  ............................. 2001-165949
Sep. 20, 2001  (JP)  ............................. 2001-286491

(51) Int. Cl.
C08G 69/26    (2006.01)
C08G 69/08    (2006.01)

(52) U.S. Cl. ....................... 528/335; 528/310

(58) Field of Classification Search ................. 528/170, 528/171, 172, 173, 174, 175, 179, 183, 185, 528/188; 562/887; 564/307, 315
See application file for complete search history.

(56) References Cited

U.S. PATENT DOCUMENTS

| 5,344,916 | A |   | 9/1994  | Harris et al. |         |
|-----------|---|---|---------|---------------|---------|
| 6,001,277 | A | * | 12/1999 | Ichimura et al. | 252/299.4 |
| 6,103,322 | A | * | 8/2000  | Gibbons et al. | 428/1.25 |
| 6,303,742 | B1 | * | 10/2001 | Okada et al.  | 528/353 |
| 6,350,845 | B1 | * | 2/2002  | Okada et al.  | 528/170 |
| 7,019,104 | B1 | * | 3/2006  | Okada et al.  | 528/229 |

FOREIGN PATENT DOCUMENTS

| JP | 58-59440 A | 4/1983 |
|----|------------|--------|
| JP | 3-59031 A | 3/1991 |
| JP | 4-7333 A | 1/1992 |
| JP | 5-203965 A | 8/1993 |
| WO | WO 01/32749 A1 | 5/2001 |

OTHER PUBLICATIONS

CAS online citation for US 6103322, [retrieved Nov. 20, 2006] AN 2000:457308,on STN, Columbus, OH, USA.*
Harris, Frank W. et al., "Synthesis of Poly(Pyridinium Salts) Containing Long Chain Alkyl Substituents", Department of Polymer Science, University of Akron, Akron, OH 44325, 2 pages.
Yim, Hyun et al., "Ultrathin Polyimide Films from Preformed Polymers," *Langmuir*, 1997, 13, 3202-3205, 4 pages.
Yim, H. et al., "Structural Study of Monolayers of Alkyl Side Chain Substituted Polyimides," *Polymer*, vol. 39, No. 19, p. 4675-4678, 1998, 4 pages.
McCreight, Kevin W. et al., "Phase Structures and Transition Behaviors in Polymers Containing Rigid Rodlike Backbones With Flexible Side Chains. V. Methylene Side-Chain Effects on Structure and Molecular Motion in a Series of Polyimides," *Journal of Polymer Sicence: Part B: Polymer Physics*, vol. 37, 1633-1646 (1999) 14 pages.
Patent Cooperation Treaty International Preliminary Examination Report (PCT Article 36 and Rule 70), From Corresponding International Application No. PCT/JP02/03710, Dated Jan. 10, 2003, 7 pages.

* cited by examiner

*Primary Examiner*—Karl Puttlitz
(74) *Attorney, Agent, or Firm*—Brinks Hofer Gilson & Lione

(57) ABSTRACT

The present invention relates to a novel diamine, a novel acid dianhydride, and a novel composition containing a polyimide produced from such diamine and acid dianhydride. Specifically, the present invention relates to an acid dianhydride that has a photosensitive group bonded through the mediation of an alkylene group or a fluoroalkylene group, a diamine that has a reactive group bonded through the mediation of an alkylene group or a fluoroalkylene group, and a polyimide composition that contains a novel polyimide having at least one of such acid dianhydride residue and diamine residue in a molecule thereof. Particularly, an object of the present invention is to provide a novel polyimide that has both photoreactivity and thermoreactivity specific to the reactive group and whose reactive group is selected from the group consisting of: organic groups derived from cinnamic acid, chalcone, furylacryloyl, benzalacetophenone, stilbene, coumarin, and pyrone; allyl; propargyl; ethinyl; $CH_2\!=\!CH\!-\!$; $CH_2\!=\!C(CH_3)\!-\!$; and skeletons derived therefrom, and it to provide a novel diamine and a novel acid dianhydride that may be contained in the polyimide composition.

4 Claims, No Drawings

DIAMINE, ACID DIANHYDRIDE, AND REACTIVE GROUP CONTAINING POLYIMIDE COMPOSITION PREPARED THEREFROM AND PROCESS OF PREPARING THEM

RELATED APPLICATIONS

This application is a nationalization of PCT Application No. PCT/JP02/03710 filed Apr. 12, 2002. This application claims priority from Japanese Patent Application No. 2001-116221 filed on Apr. 13, 2001; Japanese Patent Application No. 2001-116220 filed on Apr. 13, 2001; Japanese Patent Application No. 2001-165949 filed on May 31, 2001; and Japanese Patent Application No. 2001-286491 filed on September 20, 2001.

FIELD OF THE INVENTION

The present invention relates to a novel diamine, a novel acid dianhydride, and a composition containing a novel polyimide prepared therefrom. More particularly, the preset invention relates to an acid dianhydride having a photosensitive group bonded through an alkylene group, a diamine having a reactive group bonded through an alkylene group, and a novel polyimide composition containing at least one of the acid dianhydride and the diamine components in a molecule thereof. Particularly, the present invention relates to a novel polyimide composition having both photoreactivity and thermoreactivity specific to a reactive group selected from a skeleton derived from cinnamic acid, chalcone, furylacryloyl, benzalacetophenone, stilbene, coumarin, or pyrone, an organic group such as allyl, propargyl, ethinyl, $CH_2$=CH—, and $CH_2$=C($CH_3$)—, or a skeleton derived therefrom, and to a novel diamine and a novel acid dianhydride to be contained in the novel polyimide.

BACKGROUND OF THE INVENTION

Polyimides have been widely used, for example, in the field of electronic communication and OA appliances as well as in the field of aerospace because they have more excellent heat resistance than other organic polymers. The polyimides have recently been desired to have not only excellent heat resistance but also a variety of performance for a wide range of uses.

Photosensitive polymers can be prepared by reacting existing polymers with photosensitive groups so that the photosensitive group can function as pendant groups. A representative example of the photosensitive polymers prepared by this reaction is polyvinyl cinnamate invented by Minsk et al. of Eastman Kodak Company, which is disclosed in J. Appl. Polymer Sci., 2, 302 (1959). Polyvinyl cinnamate is prepared by the esterification of polyvinyl alcohol using cinnamic acid chloride. When this polymer is irradiated with light, it is cross-linked and cured to form cyclobutane rings.

However, polyimides with a cinnamoyl derivative skeleton at a side chain thereof are reported only in Japanese Unexamined Patent Publication No. (Patent Kokai No.)55-45747 (1980).

Since a reactive group has a double bond or triple bond, it is conceivable to introduce it into polyimide so as to use the polyimide as thermosetting resin. However, there have been few cases where a reactive group is introduced into polyimide to use the polyimide as thermosetting resin.

If a photosensitive group is introduced into at least one of an acid dianhydride component and a diamine component, cross-linking density can be increased. However, there have been only a few cases where a photosensitive group is introduced into both of them.

Further, since polyimide has a relatively high water absorption, problems may arise when it is used in the aforementioned fields, and thus it has only limited uses. In order to solve such problem, Japanese Unexamined Patent Publication No. (Patent Kokai No.) H05-346585 (1993) discloses that a fluoroalkyl group is introduced into a diamine component, and Japanese Unexamined Patent Publication No. (Patent Kokai No.) H08-220541 (1996) discloses that an alkyl group is introduced into a diamine component. However, a diamine with two groups selected from alkyl groups and fluoroalkyl groups in a molecule thereof is not known. Further, a diamine with a reactive group bonded to an end of the alkyl group or fluoroalkyl group is not also known.

An object of the present invention is to provide a novel acid dianhydride and a novel diamine with a reactive group introduced thereinto and a novel reactive group containing polyimide having the acid dianhydride and the diamine as monomer components. Specifically, an object of the present invention is to provide an acid dianhydride with a reactive group bonded through a C2 to C30 alkylene group and a C4 to C30 fluoroalkylene group, a novel diamine having two groups selected from alkylene groups having a carbon number of 6 to 30 and fluoroalkylene groups having a carbon number of 4 to 30 in a molecule thereof, and a diamine with a reactive group at the end of a side chain thereof.

Further, another object of the present invention is to provide a novel polyimide composition containing at least one of the aforementioned acid dianhydride and the diamine components in a molecule thereof. A further object of the present invention is to provide a novel polyimide composition having both photoreactivity and thermoreactivity specific to a reactive group selected from a skeleton derived from cinnamic acid, chalcone, furylacryloyl, benzalacetophenone, stilbene, coumarin, or pyrone, an organic group such as allyl, propargyl, ethinyl, $CH_2$=CH—, and $CH_2$=C($CH_3$)—, or a skeleton derived therefrom, and a novel diamine and a novel acid dianhydride to be contained in the novel polyimide.

The inventors of the present invention have studied intensively, found that their intended objects can be achieved by preparing a diamine and an acid dianhydride of a special structure and a polyimide containing such diamine and acid dianhydride, and consequently they have accomplished the present invention.

SUMMARY OF THE INVENTION

An example of an acid dianhydride according to the present invention has a side chain having a reactive group at its end through a C2 to C30 alkylene group or a C4 to C30 fluoroalkylene group.

Further, the acid dianhydride according to the present invention may have at least one aromatic group bonded to a main chain.

Further, the aforementioned reactive group can include a photosensitive group or a group that can be reacted in the presence of a photoreaction initiator.

Further, the aforementioned reactive group is a photosensitive group and can be selected from the group consisting of monovalent organic groups derived from cinnamic acid, chalcone, furylacryloyl, benzalacetophenone, stilbene, coumarin, and pyrone.

The aforementioned photoreactive group can be a group that can be reacted in the presence of a photoreaction initiator and that can contain a double bond and/or a triple bond.

The aforementioned group that contains a double bond and/or a triple bond can be a monovalent organic group selected from the group consisting of allyl, propargyl, ethinyl, $CH_2=CH—$, $CH_2=C(CH_3)—$, or groups derived therefrom.

In one embodiment, the acid dianhydride of the present invention can be represented by the general formula (1):

General formula (1)

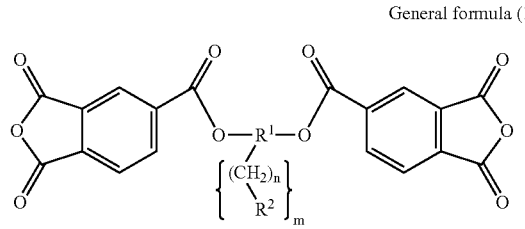

wherein $R^1$ contains a trivalent or tetravalent organic group, $R^2$ is selected from the group consisting of: monovalent organic groups derived from cinnamic acid, chalcone, furylacryloyl, benzalacetophenone, stilbene, coumarin, and pyrone; allyl; propargyl; ethinyl; $CH_2=CH—$; and $CH_2=C(CH_3)—$, n is an integer of 2 to 30, and m is an integer of 1 or 2.

In the general formula (1), $R^1$ is selected from the group consisting of:

Group (I)

(I)

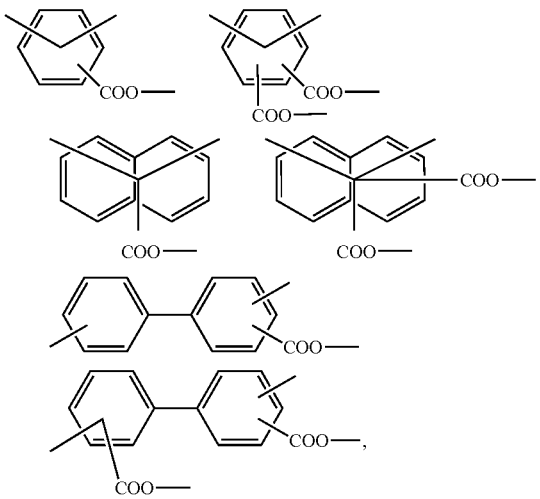

, $R^2$ is selected from the group consisting of:

Group (II)

(II)

$CH_2=CH—COO—$  $CH_2=C(CH_3)—COO—$

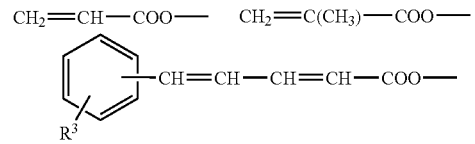

-continued

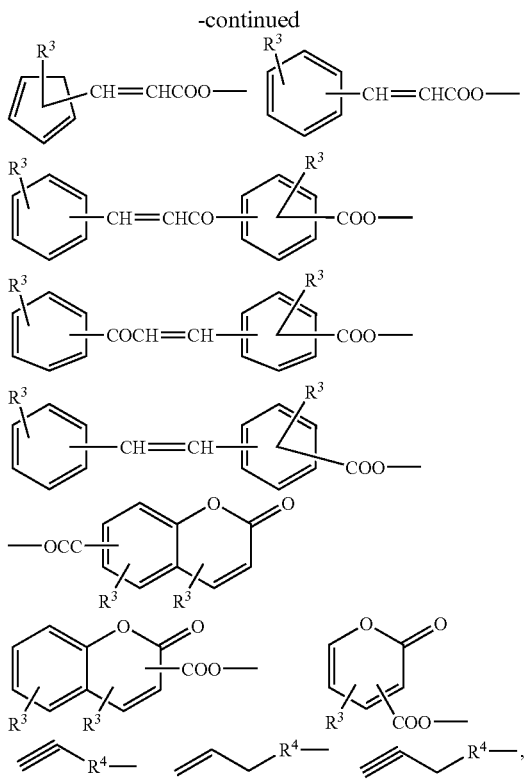

$R^3$ is selected from the group consisting of hydrogen, halogen, a methoxy group, and an alkyl group having a carbon number of 1 to 20, and $R^4$ represents —O— or —COO—.

Further, the aforementioned alkylene group can be C4 to C30, C8 to C26, or C10 to C24.

The aforementioned fluoroalkylene group can be C4 to C30, C8 to C26, or C10 to C24.

The acid dianhydride having a reactive group according to the present invention can be prepared using a diol represented by $(HO)_2—R^1—[(CH_2)_n—R^2]_m$ (wherein $R^1$ represents a trivalent or tetravalent organic group, $R^2$ represents a reactive group, n represents an integer of 2 to 30, and m represents an integer of 1 or 2) by a method comprising the step of:

(1) reacting the diol with trimellitic acid in the presence of ester catalyst; or
(2) reacting the diol with trimellitic chloride in the presence of tertiary amine.

The aforementioned reactive group can be selected from the group consisting of: monovalent organic groups derived from cinnamic acid, chalcone, furylacryloyl, benzalacetophenone, stilbene, coumarin, and pyrone; allyl; propargyl; ethinyl; $CH_2=CH—$; and $CH_2=C(CH_3)—$.

Further, an embodiment of a diamine of the present invention can have a side chain having a reactive group at its end through C2 to C30 alkylene group or C4 to C30 fluoroalkylene group.

Further, the aforementioned reactive group may contain a reactive group or a group that can be reacted in the presence of a photoreaction initiator.

Further, the aforementioned reactive group is a photosensitive group and can be a monovalent group selected from the group consisting of organic groups derived from cinnamic acid, chalcone, furylacryloyl, benzalacetophenone, stilbene, coumarin, and pyrone.

The aforementioned reactive group can be a group that can be reacted in the presence of the photoreaction initiator, and the aforementioned group that can be reacted in the presence of the photosensitive initiator can be a group having a double bond and/or a triple bond.

Further, the aforementioned group having a double bond and/or a triple bond may be a monovalent organic group selected from the group consisting of allyl, propargyl, ethinyl, $CH_2=CH-$, and $CH_2=C(CH_3)-$.

Another embodiment of diamine of the present invention can be represented by the general formula (2):

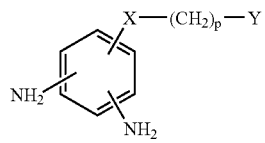

General formula (2)

wherein Y is selected from the group consisting of monovalent organic groups derived from cinnamic acid, chalcone, furylacryloyl, benzalacetophenone, stilbene, coumarin, and pyrone; allyl; propargyl; ethinyl; $CH_2=CH-$; and $CH_2=C(CH_3)-$, X represents $-O-$, $-CH_2-O-$, or $-COO-$, and p is an integer of 2 to 30.

Further, in the general formula (2), Y can be selected from the group consisting of $CH_2=CH-COO-$, $CH_2=C(CH_3)-COO$, $CH_3CH=CHCOO-$, or Group (IV)

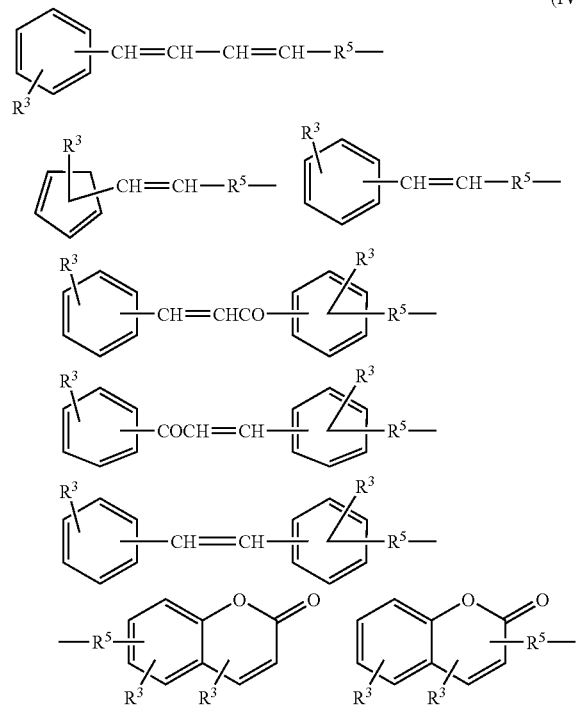

(IV)

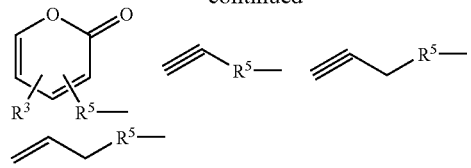

(wherein $R^3$ represents hydrogen, halogen, methoxy group, or alkyl group having a carbon number of 1 to 20 and $R^5$ represents COO—.)

Further, the aforementioned alkylene group or fluoroalkylene group can be C4 to C30, preferably C8 to C26, and more preferably C10 to C24.

The diamine of the present invention can be prepared by the method comprising the steps of:

(a) reacting $HO(CH_2)_p-Br$ (wherein p is an integer of 2 to 30) with metal salt containing a reactive group in an aprotic polar solvent; and (b)(i) reacting the reaction product prepared by the step of (a) with dinitrobenzoic acid in the presence of an esterification catalyst, or (ii) reacting the reaction product prepared by the step of (a) with dinitrobenzoyl chloride in the presence of tertiary amine.

Further, the aforementioned reactive group can be selected from the group consisting of monovalent organic groups derived from cinnamic acid, chalcone, furylacryloyl, benzalacetophenone, stilbene, coumarin, and pyrone; allyl; propargyl; ethinyl; $CH_2=CH-$; and $CH_2=C(CH_3)-$.

Further, a further embodiment of the diamine of the present invention can have two C6 to C30 alkylene groups in a molecule thereof and reactive groups at the end of the alkylene groups.

Further, the diamine of the present invention can have two C4 to C30 fluoroalkylene groups in a molecule thereof and reactive groups at the end of the fluoroalkylene groups.

The diamine of the present invention can have two alkylene groups in a molecule thereof through an ester bond and/or an ether bond.

A still further embodiment of the diamine of the present invention can be represented by the general formula (3):

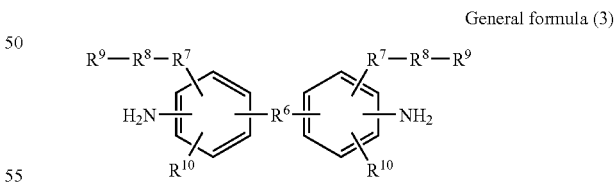

General formula (3)

(wherein $R^6$ represents a divalent organic group selected from the group consisting of a single bond, $-O-$, $-SO_2-$, $-C(=O)-$, $(CH_2)_q-$, and

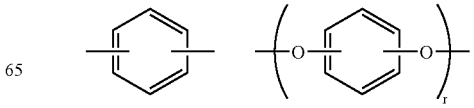

-continued

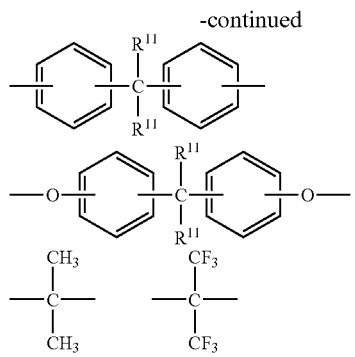

(wherein q is an integer of 1 to 30, r is an integer of 1 to 3, $R^{11}$ represents hydrogen, methyl, trifluoromethyl, or benzene); $R^7$ represents —O—, —COO—, or —NHCO—; $R^8$ represents an alkylene group having a carbon number of 6 to 30 and/or a fluoroalkylene group having a carbon number of 4 to 30; $R^9$ is selected from the group consisting of monovalent organic groups derived from cinnamic acid, chalcone, furylacryloyl, benzalacetophenone, stilbene, coumarin, and pyrone; allyl; propargyl; ethinyl; $CH_2$=CH—; and $CH_2$=C($CH_3$)—; and $R^{10}$ represents hydrogen, C1 to $C_{10}$ alkyl group, C1 to C6 fluoroalkyl group, methoxy group, ethoxy group, butoxy group, or halogen.)

Further, the diamine of the present invention can be prepared by the method comprising the steps of: (a) protecting an amino group of diamine represented by the following formula

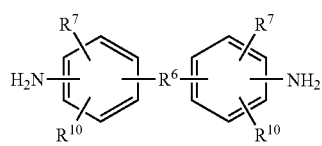

(wherein $R^6$ is a divalent organic group, $R^{10}$ represents hydrogen, C1 to $C_{10}$ alkyl group, C1 to C6 fluoroalkyl group, methoxy group, ethoxy group, butoxy group or halogen, and $R^7$ represents COOH and/or OH) by the use of a protective group; (b) reacting the diamine wherein $R^7$ in the above-described formula is metal salt with alkyl halide or fluoroalkyl halide represented by

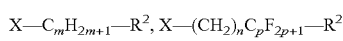

X—$C_mH_{2m+1}$—$R^2$, X—$(CH_2)_nC_pF_{2p+1}$—$R^2$ (wherein X represents bromine, chlorine, or iodine, m is an integer of 6 to 30, n is an integer of 1 to 10, and p is an integer of 4 to 30) in an aprotic solvent to prepare a compound with a photosensitive group and alkylene or fluoroalkylene group introduced thereto; and (c) removing the protective group for the amino group to prepare a diamine.

Alternatively, the diamine of the present invention can be prepared by the method comprising the steps of: (a) preparing a compound by protecting an amino group of diamine represented by the general formula (4):

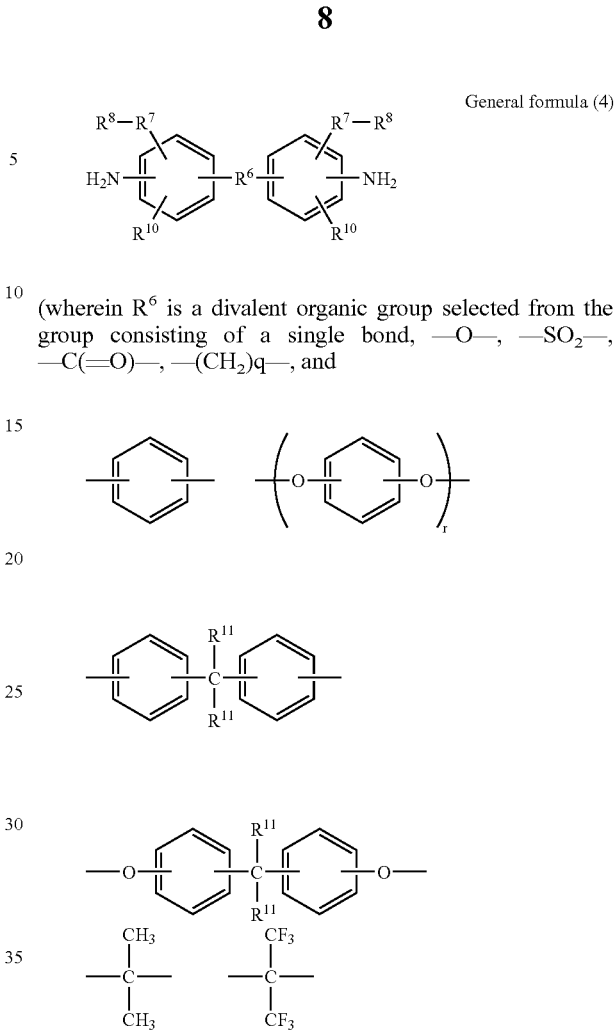

(wherein $R^6$ is a divalent organic group selected from the group consisting of a single bond, —O—, —$SO_2$—, —C(=O)—, —$(CH_2)q$—, and (wherein q is an integer of 1 to 30, r is an integer of 1 to 3, $R^{11}$ represents hydrogen, methyl, trifluoromethyl, or benzene); $R^7$ represents —O—, —COO—, or —NHCO—; $R^8$ represents an alkyl group having a carbon number of 6 to 30 and/or a fluoroalkylene group having a carbon number of 4 to 30; $R^{10}$ represents hydrogen, C1 to C10 alkyl group, C1 to C6 fluoroalkyl group, methoxy group, ethoxy group, butoxy group, or halogen) by the use of a protective group; (b) reacting a halide or ester having a reactive group with the compound prepared by the step (a); and (c) removing the protective group for the amino group.

In the aforementioned method, the reactive group can be selected from the group consisting of: monovalent organic groups derived from cinnamic acid, chalcone, furylacryloyl, benzalacetophenone, stilbene, coumarin, and pyrone; allyl; propargyl; ethinyl; $CH_2$=CH—; and $CH_2$=C($CH_3$)—.

The aforementioned diamine can be represented by the general formula (4):

General formula (4)

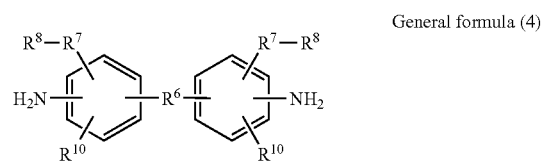

(wherein $R^6$ is a divalent organic group selected from the group consisting of: a single bond, —O—, —SO$_2$—, —C(=O)—, (CH$_2$)q—, and

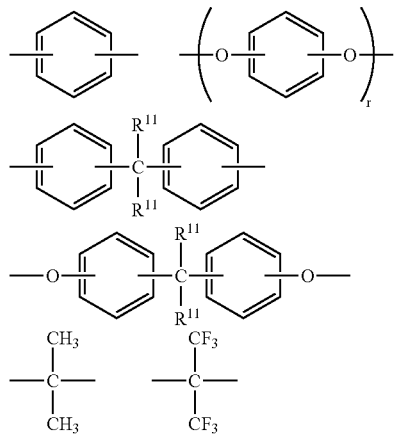

(wherein q is an integer of 1 to 30, r is an integer of 1 to 3, $R^{11}$ represents hydrogen, methyl, trifluoromethyl, or benzene); $R^7$ represents —O—, —COO—, or —NHCO—; $R^8$ represents a C6 to C30 alkyl group and/or a C4 to C30 fluoroalkylene group; $R^{10}$ represents hydrogen, C1 to C10 alkyl group, C1 to C6 fluoroalkyl group, methoxy group, ethoxy group, butoxy group, or halogen).

A polyimide composition of the present invention can contain polyimide having in a molecule at least one of an acid dianhydride component having a reactive group through C2 to C30 alkylene group and C4 to C30 fluoroalkylene group and a diamine component having a reactive group through C2 to C30 alkylene group or C4 to C30 fluoroalkylene group.

The aforementioned reactive group can be selected from the group consisting of: monovalent organic groups derived from cinnamic acid, chalcone, furylacryloyl, benzalacetophenone, stilbene, coumarin, and pyrone; allyl; propargyl; ethinyl; CH$_2$=CH—; and CH$_2$=C(CH$_3$)—

Further, another embodiment of the polyimide composition according to the present invention can contain polyimide having in a molecule an acid dianhydride component represented by the general formula (1):

General formula (1)

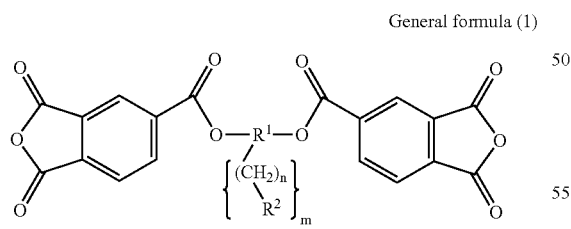

wherein $R^1$ contains a trivalent or tetravalent organic group; $R^2$ is selected from the group consisting of: monovalent organic groups derived from cinnamic acid, chalcone, furylacryloyl, benzalacetophenone, stilbene, coumarin, and pyrone; allyl; propargyl; ethinyl; CH$_2$=CH—; and CH$_2$=C(CH$_3$)—; n is an integer of 2 to 30, and m is an integer of 1 or 2.

In the aforementioned general formula (1), $R^1$ is selected from the group consisting of:

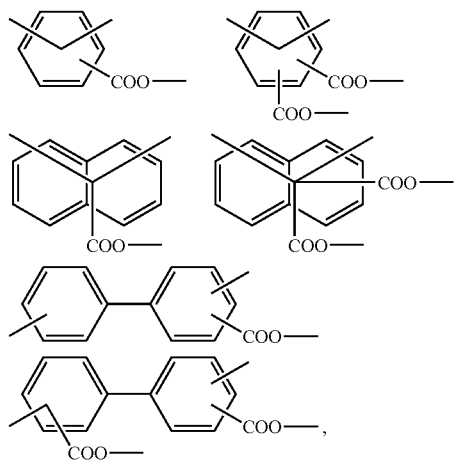

$R^2$ is selected from the group consisting of:

CH$_2$=CH—COO—    CH$_2$=C(CH$_3$)—COO—

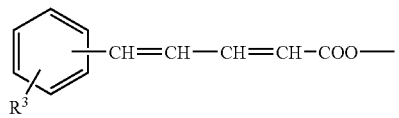

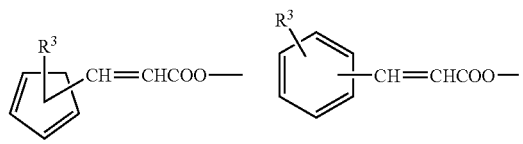

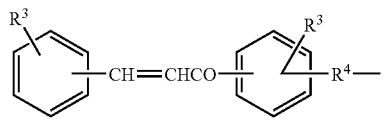

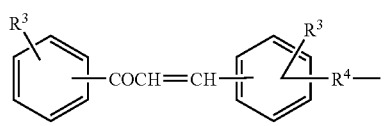

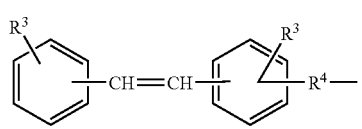

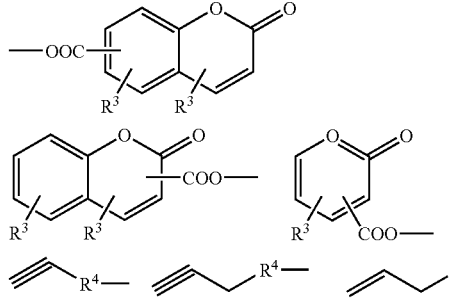

$R^3$ is selected from the group consisting of: hydrogen, halogen, methoxy group and alkyl group having a carbon number of 1 to 20, and $R^4$ represents —O— or —COO—.

A further embodiment of the polyimide composition of the present invention can contain polyimide having a diamine component represented by the general formula (2):

General formula (2)

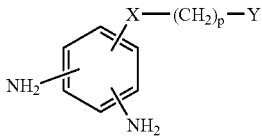

wherein Y is selected from the group consisting of: monovalent organic groups derived from cinnamic acid, chalcone, furylacryloyl, benzalacetophenone, stilbene, coumarin, and pyrone; allyl; propargyl; ethinyl; $CH_2\!=\!CH\!-\!$; and $CH_2\!=\!C(CH_3)\!-\!$, X represents $-O-$, $-CH_2-O-$, or $-COO-$, and p is an integer of 2 to 30.

A further embodiment of the polyimide composition of the present invention can contain polyimide having, in a molecule, a diamine component represented by the general formula (3):

General formula (3)

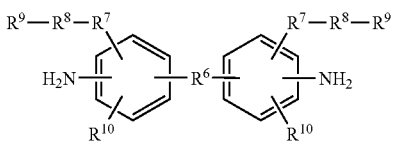

(wherein $R^6$ is a divalent organic group selected from the group consisting of: a single bond, $-O-$, $-SO_2-$, $-C(=O)-$, $(CH_2)q-$, and

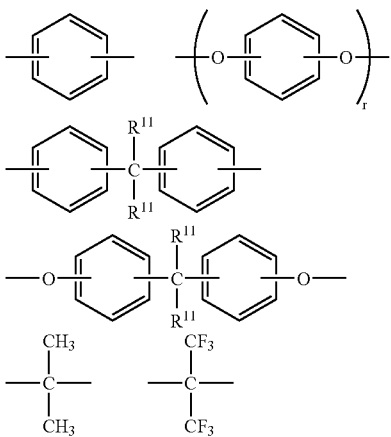

(wherein q is an integer of 1 to 30, r is an integer of 1 to 3, $R^{11}$ represents hydrogen, methyl, trifluoromethyl, or benzene); $R^7$ represents $-O-$, $-COO-$, or $-NHCO-$; $R^8$ represents a C6 to C30 alkyl group and/or a C4 to C30 fluoroalkyl group; $R^9$ is selected from the group consisting of: monovalent organic groups derived from cinnamic acid, chalcone, furylacryloyl, benzalacetophenone, stilbene, coumarin, and pyrone; allyl; propargyl; ethinyl; $CH_2\!=\!CH\!-\!$; and $CH_2\!=\!C(CH_3)\!-\!$; and $R^{10}$ represents hydrogen, C1 to $C_{10}$ alkyl group, C1 to C6 fluoroalkyl group, methoxy group, ethoxy group, butoxy group, or halogen.)

DESCRIPTION OF THE PREFERRED EMBODIMENTS

In this specification, the term "reactive group" includes a photosensitive group and a group that can be reacted in the presence of a photoreaction initiator. The term "photosensitive group" means a group that is excited by electromagnetic wave and that is chemically and structurally changed in its molecule or between its molecules. More preferably the photosensitive group means a group that is excited by electromagnetic wave classified into a category ranging from near ultraviolet light to visible ray (having a wavelength of 290 to 430 nm) and that can be cross-linked between its molecules and/or dimerized.

The term "group that can be reacted in the presence of a photoreaction initiator" means a reactive group that can be cross-linked in the presence of such photoreaction initiator that generates a radical by the use of light even if it does not have photosensitivity, for example. Examples of such groups include: allyl having a double bond or a triple bond, propargyl, ethinyl, $CH_2\!=\!CH\!-\!$, and $CH_2\!=\!C(CH_3)\!-\!$. Since the group that is reacted in the presence of a photoreaction initiator is also cross-linked and/or dimerized by means of light in the presence of the photoreaction initiator, it can produce the same effects as the photosensitive group. For example, cinnamic acid is a compound having photosensitivity. In this specification, not only the diamines having a photosensitive group according to the present invention but the polyimides prepared by the polymerization with such diamines also have photosensitivity.

The present invention can provide a novel acid dianhydride and a novel diamine that have a reactive group having, through an alkylene group or fluoroalkylene group, a photosensitive group selected from an organic group derived from cinnamic acid, chalcone, furylacryloyl, benzalacetophenone, stilbene, coumarin, or pyrone; allyl; propargyl; ethinyl; $CH_2\!=\!CH\!-\!$; $CH_2\!=\!C(CH_3)\!-\!$; or a skeleton derived therefrom and that have photoreactivity and thermoreactivity specific to the reactive group, and can provide a novel polyimide composition that is prepared from the above acid dianhydride and diamine and that has both photoreactivity and thermoreactivity specific to the reactive group.

Although the acid dianhydride of the present invention is not particularly limited as far as it has a photosensitive group through C2 to C30 alkylene group or C4 to C30 fluoroalkylene group, a preferable example of the acid dianhydride is synthesized by the following method.

A preferable acid dianhydride can be represented by the following general formula (1):

General formula (1)

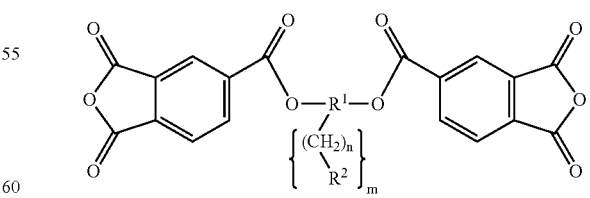

wherein $R^1$ has a trivalent or tetravalent organic group, $R^2$ is selected from the group consisting of: monovalent organic groups derived from cinnamic acid, chalcone, furylacryloyl, benzalacetophenone, stilbene, coumarin, and pyrone; allyl; propargyl; ethinyl; $CH_2\!=\!CH\!-\!$; and $CH_2\!=\!C(CH_3)\!-\!$, n is an integer of 2 to 30, and m is an integer of 1 or 2. As far as n is in a range of an integer of 2 to 30, it is not particularly limited. Preferably, n is an integer of 6 to 26, and more preferably an integer of 10 to 24. When n is smaller than an integer of 2, the acid dianhydride tends to have poor water absorption and poor dielectric property. On the contrary, when n is bigger than an integer of 30, the acid dianhydride tends to have poor heat resistance.

In the present invention, $R^1$ is a trivalent or tetravalent aromatic organic group. When $R^1$ is a trivalent aromatic group, one of the bonds is an ester bond. When $R^1$ is a tetravalent aromatic group, two of the bonds are enter bonds. Specifically, $R^1$ is represented by the following group (I):

Group (I)

(I)

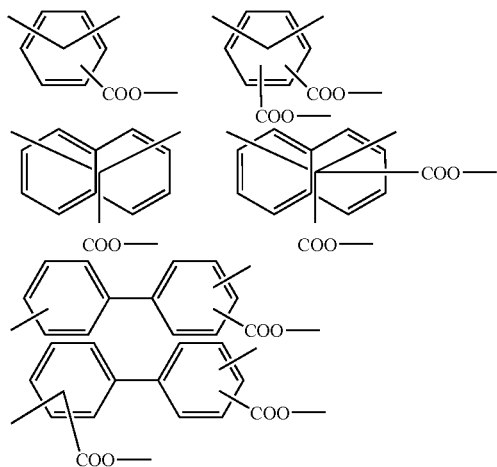

wherein $R^2$ is represented by the following group (II)

Group (II)

(II)

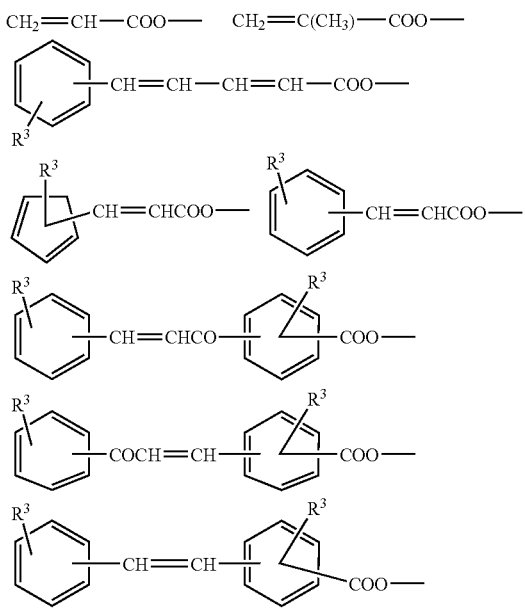

-continued

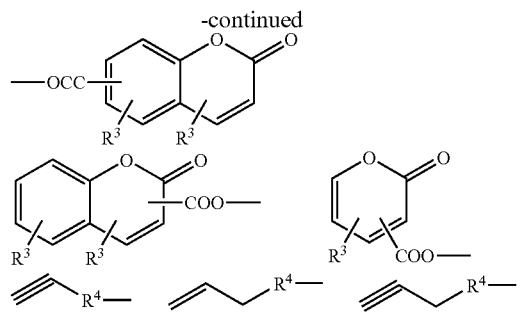

(wherein $R^3$ is hydrogen, halogen, a methoxy group, and an alkyl group having a carbon number of 1 to 20, and $R^4$ represents —O— or —COO—.)

Next, a method of synthesizing an acid dianhydride represented by the general formula (1) will be concretely described.

The acid dianhydride represented by the general formula (1) can be prepared using diol represented by the general formula (5):

$$(HO)_2-R^1-[(CH_2)n-R^2]_m \qquad \text{General formula (5)}$$

by a method comprising the steps of: (1) reacting the diol with trimellitic acid in the presence of ester catalyst; or (2) reacting the diol with trimellitic chloride in the presence of tertiary amine.

In the general formula (5), $R^1$ represents a trivalent or tetravalent organic group, R is a reactive group selected from the group consisting of: monovalent organic groups derived from cinnamic acid, chalcone, furylacryloyl, benzalacetophenone, stilbene, coumarin, and pyrone; allyl; propargyl; ethinyl; $CH_2=CH-$; $CH_2=C(CH_3)-$; and skeletons derived therefrom, n is an integer of 2 to 30, and m is an integer of 1 or 2.

In the general formula (5), it is preferable to synthesize a site represented by $[(CH_2)_n-R^2]_m$ first.

For example, $Br[((CH_2)_n-R^2]_m$ can be prepared by:
(i) reacting $Br(CH_2)_nOH$ with carboxylic acid selected from the group represented by the group (III):

Group (III)

(III)

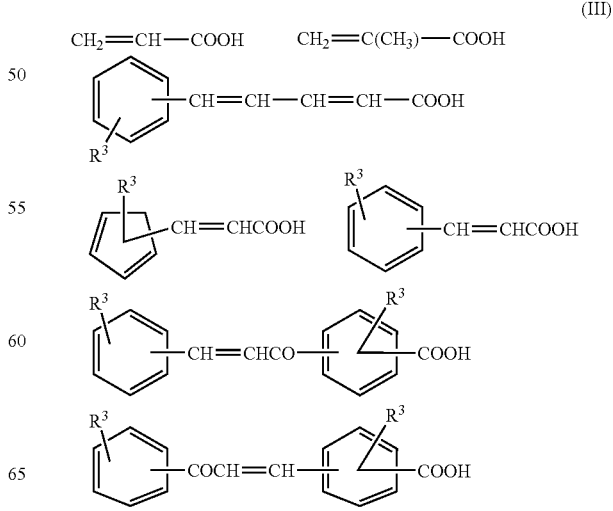

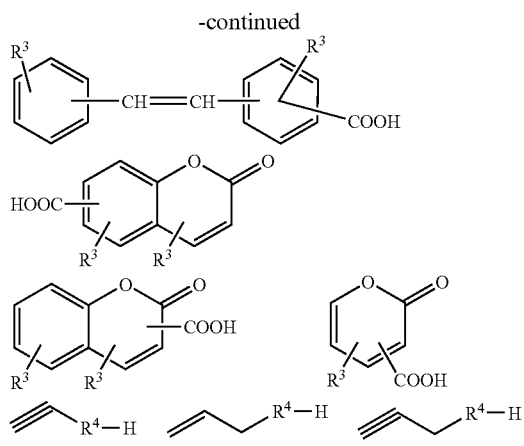

(wherein R³ represents hydrogen, halogen, a methoxy group, or an alkyl group having a carbon number of 1 to 20, and R⁴ represents —O— or —COO—) in the presence of esterification catalyst; or (ii) reacting Br(CH₂)ₙOH with acid chloride corresponding to the aforementioned carboxylic acid in the presence of tertiary amine. Instead of Br, other halogens can be used to produce the same reaction.

Next, $(HO)_2-R^1-[COO(CH_2)_n-R^2]_m$, which corresponds to the general formula (5), is prepared by reacting $(HO)_2-R^{1'}-[COOCs]_m$ and $Br[(CH_2)_n-R^2]_m$.

Instead of Cs, other alkali metal salts can be used to produce the same effect. However, m is an integer of 1 or 2.

In the general formula (1), R¹ is preferably selected from the group (I):

Group (I)

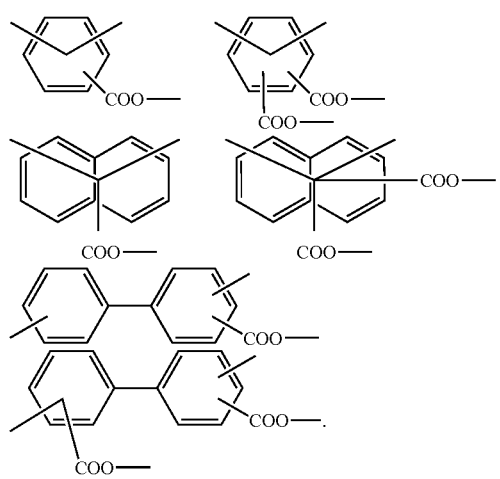
(I)

In the general formula (1), R² is preferably selected from the group (II):

Group (II)

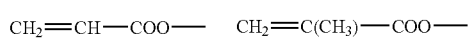
(II)

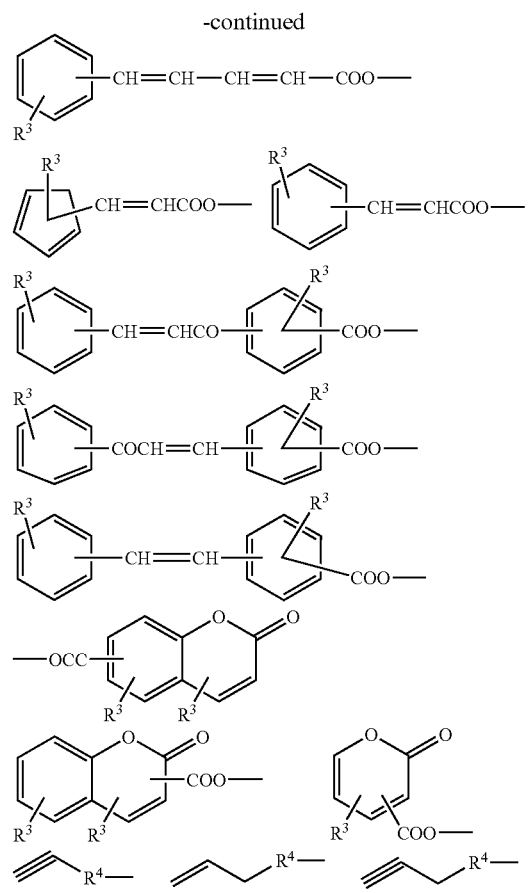

(wherein R³ represents hydrogen, halogen, a methoxy group, and an alkyl group having a carbon number of 1 to 20, and R⁴ represents —O— or —COO—.)

Next, the diamine of the present invention contains a reactive group through a C2 to C30 alkylene group. The reactive group is a monovalent organic group derived from cinnamic acid, chalcone, furylacryloyl, benzalacetophenone, stilbene, coumarin, or pyrone; allyl; propargyl; ethinyl; CH₂=CH—; CH₂=C(CH₃)—; or a skeleton derived therefrom, and the diamine of the present invention has both photoreactivity specific to a reactive group and thermoreactivity.

For example, the diamine of the present invention can be represented by the general formula (2):

General formula (2)

$$\text{NH}_2-\text{C}_6\text{H}_3(\text{NH}_2)-X-(CH_2)_p-Y$$

(2)

wherein Y is selected from the group consisting of: monovalent organic groups derived from cinnamic acid, chalcone, furylacryloyl, benzalacetophenone, stilbene, coumarin, and pyrone; allyl; propargyl; ethinyl; CH₂=CH—; and CH₂=C(CH₃)—, X represents —O—, —CH₂—O—, or —COO—, and p is an integer of 2 to 30.

Particularly, in the general formula (2), Y is preferably a monovalent organic group selected from $CH_2$=CHCOO—, $CH_2$=C($CH_3$)—CHCOO—, $CH_3$CH=CHCOO—, or the following group (IV):

Group (IV)

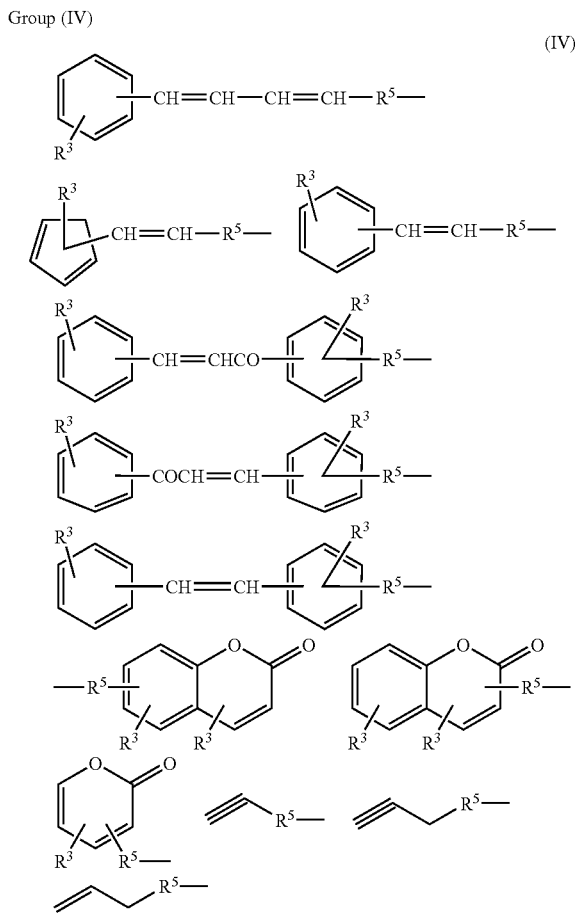

(wherein $R^3$ is hydrogen, halogen, methoxy group or alkyl group having a carbon number of 1 to 20, and $R^5$ represents COO—.)

In another embodiment, the aforementioned alkylene group can be C4 to C30, preferably C8 to C26, and more preferably C10 to C24.

Although a method of synthesizing a compound using cinnamic acid will be described below as an example, other reactive groups can also be used instead of cinnamic acid.

$HO(CH_2)_n Br$ is reacted with cesium salt of cinnamic acid in an aprotic polar solvent such as n-methylpyrrolidone to prepare

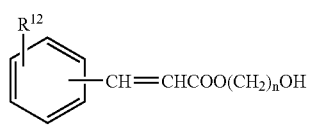

(wherein $R^{12}$ represents hydrogen, halogen, methoxy group or alkyl group having a carbon number of 1 to 20.)

The aforementioned compound is reacted with dinitrobenzoic acid in the presence of esterification catalyst or with dinitrobenzoyl chloride in the presence of tertiary amine to prepare a dinitro compound represented by

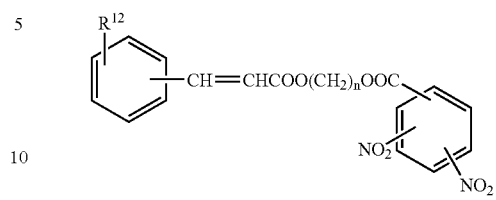

(wherein $R^{12}$ represents hydrogen, halogen, methoxy group or alkyl group having a carbon number of 1 to 20.)

The aforementioned dinitro compound is reduced to prepare a diamine represented by the general formula (2) wherein X represents COO.

Next, the case where X in the general formula (2) represents —$CH_2$—O— will be described.

Dinitrobenzyl alcohol and $HO(CH_2)_n Br$ are reacted in an aprotic solvent such as N-dimethylformamide in the presence of a base such as sodium carbonate to prepare

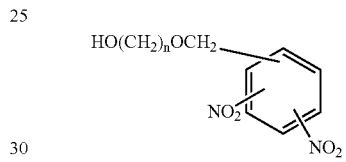

The aforementioned compound is reacted with cinnamic acid in the presence of esterification catalyst or with chloride cinnamate in the presence of tertiary amine to prepare the following dinitro compound:

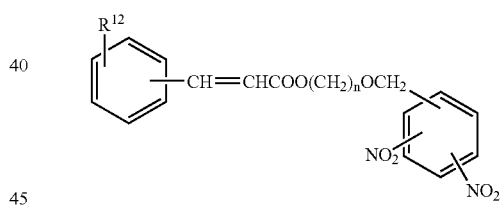

(wherein $R^{12}$ represents hydrogen, halogen, methoxy group, or alkyl group having a carbon number of 1 to 20.)

The aforementioned compound is reduced to prepare diamine represented by the general formula (2) wherein X is —$CH_2$—O—.

A starting material is dinitrobenzyl alcohol where X in the general formula (2) is —$CH_2$—O—. However, when dinitrophenol is used as a starting material, diamine represented by the general formula (2) wherein X is —O— can be prepared.

In the general formula (2), n is an integer of 2 to 30, preferably an integer of 6 to 26, and more preferably an integer of 10 to 24. When n is smaller than an integer of 2, the diamine tends to have poor water absorption and poor dielectric property. On the contrary, when n is bigger than an integer of 30, the diamine tends to have poor heat resistance.

Next, reducing conditions will be described.

A desired diamine can be prepared by Bechamp reduction of the aforementioned dinitro compound or by hydrogenation using Pd-carbon black catalyst or Pt-carbon black catalyst which is inactivated by adding iron or sulfur.

In this specification, the term "Pt-carbon black" is a catalyst having platinum supported on a carrier of carbon black, and the term "Pd-carbon black" is a catalyst having palladium supported on a carrier of carbon black. As such kinds of catalysts, it is general to use catalysts having precious metal supported on a carrier of activated carbon. When activated carbon is used as a carrier, a proportion of reduction of double bonds of cinnamic acid is larger than when carbon black is used as a carrier. Therefore, it is preferred to use a catalyst with a carrier of carbon black. However, a catalyst with a carrier of activated carbon can inhibit the reduction of double bonds of cinnamic acid and can preferentially reduce a nitro group, when more poisoning material is mixed into the catalyst with a carrier of activated carbon than a catalyst with a carrier of carbon black. For example, when Fe or Na is mixed into a catalyst having platinum supported on a carrier of activated carbon, this catalyst exhibits the same reduction selectivity to a nitro group as Pt-carbon black catalyst.

The reduction conditions of the dinitro compound will be described below. The aforementioned dinitro compound has double bonds of cinnamoyl skeleton. Therefore, under a strict reduction condition, the double bonds are undesirably reduced. Under a strict acidic condition, there is high possibility that ester bonds are decomposed. Furthermore, under an alkaline condition, there is possibility that the Michael addition reaction may occur. For this reason, the reduction conditions must be set up adequately.

A suitable method for reducing the dinitro compound is hydrogeneration in an organic solvent using a Pd-carbon black catalyst deactivated by adding iron, sulfur, and the like, and a Pt-carbon black catalyst. Since the Pd-carbon black catalyst generally used in hydrogeneration has high reactivity, an undesired reduction of double bonds may be easily caused. Therefore, it is necessary to use a Pd-carbon black catalyst whose reactivity is deactivated by iron, sulfur, and the like. The Pt-carbon black catalyst is desirably used in this reduction system, because it inhibits the reduction of double bonds, gives a higher priority to a reduction of nitro groups than a reduction of double bonds, and produces a desired diamine in high yield. The same result can be obtained using Pt-carbon black catalyst with Fe and Na mixed thereinto.

In the Pt-carbon black catalyst, a platinum concentration is about 0.1 to 40% by weight. As far as the platinum concentration is 0.1% by weight or more, catalytic effects can be produced. A reaction rate tends to increase with the concentration of platinum. Considering that platinum is a precious metal, the platinum concentration in a catalyst is preferably 1 to 20% by weight. Likewise, in the Pd-carbon black catalyst, a palladium concentration is about 0.1 to 40% by weight, and catalytic effects can be produced as far as the palladium concentration is 0.1% by weight or more. A reaction rate tends to increase with the concentration of palladium. Considering that palladium is a precious metal, the palladium concentration in a catalyst is preferably 1 to 30% by weight. Both Pt-carbon black and Pd-carbon black can produce the same effects in the dry state or in the water-absorbed. Industrially, the water-absorbed state is preferable for preventing dust from rising and for easy handling.

Examples of solvents to be used in reduction include: alcohols; dioxane; aromatic solvents such as toluene and xylene; sulfoxide solvents such as dimethyl sulfoxide and diethyl sulfoxide; formamide solvents such as N,N-dimethylformamide and N,N-diethylformamide; acetamide solvents such as N,N-dimethylacetamide and N,N-diethylacetamide; pyrrolidone solvents such as N-methyl-2-pyrrolidone and N-vinyl-2-pyrrolidone; phenol solvents such as phenol, o-cresol, m-cresol, p-cresol, xylenol, phenol halide, and catechol; hexamethylphosphoramide; and γ-butyrolactone. Any solvent can be used, as far as it does not inhibit the reduction reaction and can dissolve diamine and dinitro compound.

The Bechamp reduction is carried out by adding a dinitro compound and Fe powder to a solvent and heating the solvent at 130° C. or less. Although the aforementioned solvents can be used, preferable solvents are acetic acid, alcohols, dioxane, or the like.

Further, another embodiment of the diamine having a reactive group according to the present invention is represented by the general formula (3):

General formula (3)

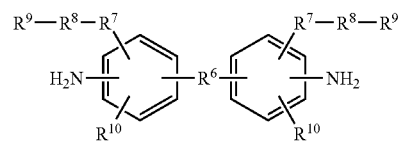

(wherein $R^6$ is a divalent organic group selected from the group consisting of: a single bond, —O—, —SO$_2$—, —C(=O)—, —(CH$_2$)q—,

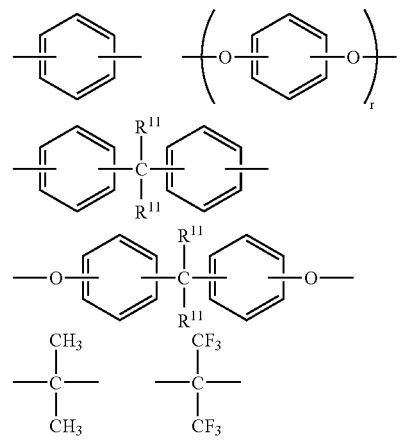

(wherein q is an integer of 1 to 30, r is an integer of 1 to 3, $R^{11}$ represents hydrogen, methyl, trifluoromethyl, or benzene); $R^7$ represents —O—, —COO—, or —NHCO—; $R^8$ represents an alkyl group having a carbon number of 6 to 30 and/or a fluoroalkylene group having a carbon number of 4 to 30; $R^9$ is selected from the group consisting of monovalent organic groups derived from cinnamic acid, chalcone, furylacryloyl, benzalacetophenone, stilbene, coumarin, and pyrone; allyl; propargyl; ethinyl; CH$_2$=CH—; and CH$_2$=C(CH$_3$)—; X represents —O—, —CH$_2$—O—, or —COO—; and $R^{10}$ represents hydrogen, C1 to C$_{10}$ alkyl group, C1 to C6 fluoroalkyl group, methoxy group, ethoxy group, butoxy group, or halogen.)

Next, a method of synthesizing diamine will be concretely described.

First, an amino group of the diamine is protected. In this case, any protective groups for amino groups can be used. Examples of protective groups include: a benzyloxycarbonyl group, 9-fluorenyl methoxycarbonyl group, t-butoxycarbonyl group, 9-fluorenyl methoxycarbonyl group, and methylcarbonyl group. A particularly preferable protective group is a t-butoxycarbonyl group. A reaction caused by the introduction of a protective group will be described by taking a reaction caused in the introduction of t-butoxycarbonyl group as an example.

A diamine represented by the following formula:

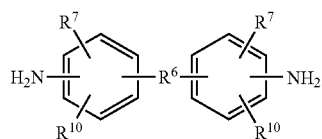

(wherein $R^6$ is a divalent organic group, $R^{10}$ represents hydrogen, C1 to C10 alkyl group, C1 to C6 fluoroalkyl group, methoxy group, ethoxy group, butoxy group, or halogen, and $R^7$ represents COOH and/or OH) and

$(CH_3)_3COOCOCOOC(CH_3)_3$ are reacted to protect an amino group.

Following is a reaction formula:

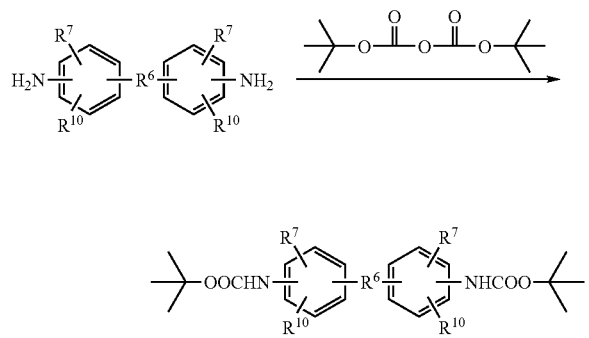

(wherein $R^6$ is a divalent organic group, $R^{10}$ represents hydrogen, C1 to C10 alkyl group, C1 to C6 fluoroalkyl group, methoxy group, ethoxy group, butoxy group, or halogen, and $R^7$ represents COOH and/or OH.)

When $R^7$ is COOH, they must be reacted in alkali conditions. Particularly, it is preferred to use metal carbonate to obtain metal salt of

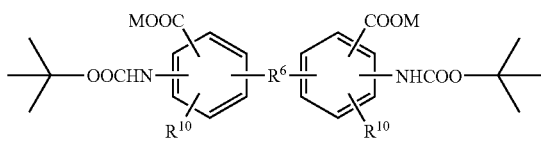

(wherein $R^6$ is a divalent organic group, $R^{10}$ represents hydrogen, C1 to $C_{10}$ alkyl group, C1 to C6 fluoroalkyl group, methoxy group, ethoxy group, butoxy group, or halogen, and M represents an alkali metal.)

Further, in order to prevent the decomposition of di-t-butyldicarbonate $(((CH_3)_3C—O—CO)_2O)$, they are reacted at 50° C. or less, preferably at 0 to 40° C. A desired t-butoxycarbonyl group can be introduced by such reaction.

A compound represented by the following chemical formula:

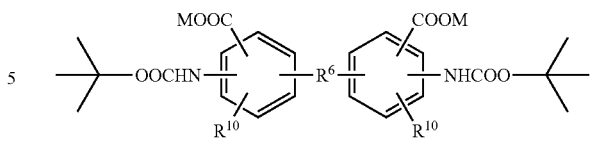

and alkyl halide or fluoroalkyl represented by $X—C_mH_{2m+1}$ or $X—(CH_2)_nC_pF_{2p+1}$ (wherein X represents bromine, chlorine, or iodine, m is an integer of 6 to 30, n is an integer of 1 to 10, and p is an integer of 4 to 30) are reacted in an aprotic solvent to prepare a compound represented by the following general formula:

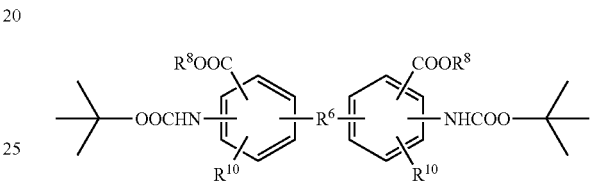

(wherein $R^6$ is a divalent organic group, $R^{10}$ represents hydrogen, C1 to $C_{10}$ alkyl group, C1 to C6 fluoroalkyl group, methoxy group, ethoxy group, butoxy group, or halogen, $R^8$ represents an alkyl group represented by $C_mH_{2n+1}$ and/or fluoroalkyl represented by $(CH_2)_nC_pF_{2p+1}$ wherein m is an integer of 6 to 30, p is an integer of 4 to 30, and n is an integer of 1 to 10.)

A protective group of the aforementioned compound is removed to prepare a diamine represented by the general formula (4). For example, a t-butoxycarbonyl group can be easily decomposed and removed by the addition of an acid. When the t-butoxycarbonyl group is mixed with, for example, trifluoroacetic acid at a room temperature, it is decomposed for a few minutes to an hour. When it is neutralized with alkali, a novel diamine represented by the general formula (4):

(4)

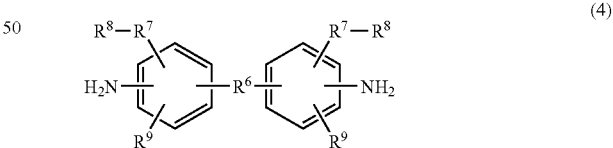

General Formula (4)

which has two long-chain alkyl groups or fluoroalkyl groups in its molecular. The aforementioned diamine can be prepared by mixing and heating hydrochloric acid and a solvent such as dioxane for neutralization.

The diamine represented by the general formula (4) whose amino group is protected by a protective group is reacted with carboxylic acid having a photosensitive group represented by: $CH_2$=CH—COO—, $CH_2$=C($CH_3$)—COO—, $CH_3CH$=CHCOO—, or Group IV

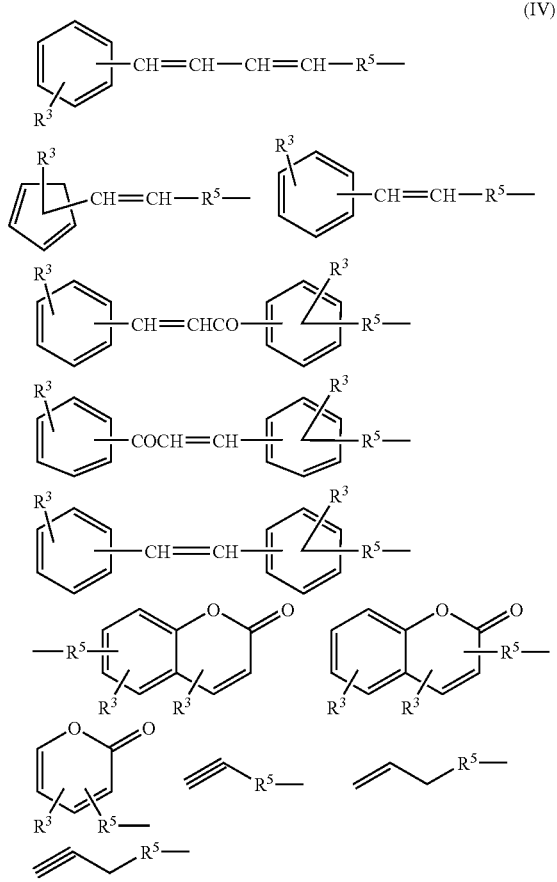

(IV)

(wherein $R^3$ represents hydrogen, halogen, methoxy group, or alkyl group having a carbon number of 1 to 20, and $R^5$ represents COO—) in the presence of ester catalyst, or reacted with carboxylic acid chloride having the aforementioned photosensitive group in the presence of tertiary amine to prepare a diamine compound represented by the general formula (3) whose amino group is protected.

The diamine represented by the general formula (3) can be prepared by removing the protective group from this compound.

Further, the diamine represented by the general formula (3) can be prepared by the following synthesizing method. Metal salt of diamine with amino group protected by a protective group represented by

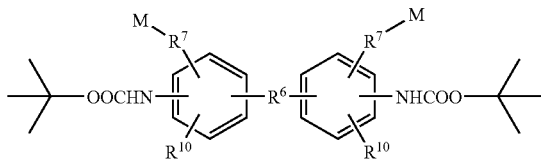

(wherein $R^6$ is a divalent organic group, $R^7$ represents —O—, COO—, or —NHCO—, $R^{10}$ represents hydrogen, C1 to $C_{10}$ alkyl group, C1 to C6 fluoroalkyl group, methoxy group, ethoxy group, butoxy group, or halogen, and M represents alkali metal) is reacted with alkyl halide represented by

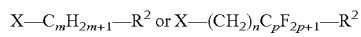

(wherein X represents bromine, chlorine, or iodine, m is an integer of 6 to 30, n is an integer of 1 to 10, and p is an integer of 4 to 30) or fluoroalkyl in an aprotic solvent to prepare a compound with a photosensitive group and alkylene group or fluoroalkylene group introduced thereinto.

Then, the protective group is removed from the compound to prepare a novel diamine having a long-chain alkylene group with a reactive group at its end or a fluoroalkylene group at its side chain as represented by the general formula (3):

General formula (3)

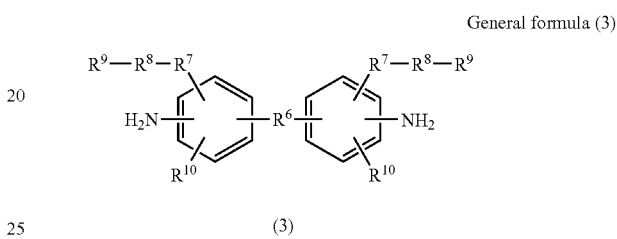

(3)

(wherein $R^6$ is a divalent organic group selected from the group consisting of a single bond, —O—, —SO$_2$—, —C(=O)—, (CH$_2$)q—,

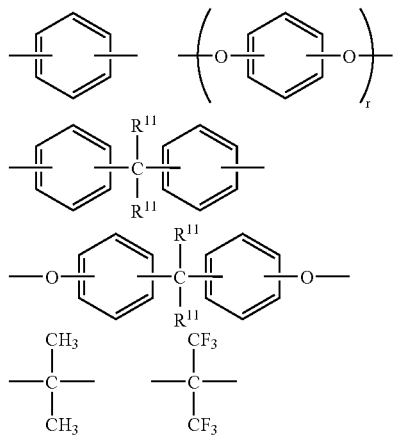

(wherein q is an integer of 1 to 30, r is an integer of 1 to 3, $R^{11}$ represents hydrogen, methyl, trifluoromethyl, or benzene); $R^7$ represents —O—, —COO—, or —NHCO—; $R^8$ represents an alkylene group having a carbon number of 6 to 30 and/or a fluoroalkylene group having a carbon number of 4 to 30; $R^9$ is selected from the group consisting of monovalent organic groups derived from cinnamic acid, chalcone, furylacryloyl, benzalacetophenone, stilbene, coumarin, and pyrone; allyl; propargyl; ethinyl; CH$_2$=CH—; and CH$_2$=C(CH$_3$)—; X represents —O—, —CH$_2$—O—, or —COO—; and $R^{10}$ represents hydrogen, C1 to C10 alkyl group, C1 to C6 fluoroalkyl group, methoxy group, ethoxy group, butoxy group, or halogen.) Examples of carboxylic acid having a reactive group are shown by the aforementioned group (III).

The compound represented by

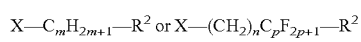

can be prepared by reacting carboxylic acid having a photosensitive group with

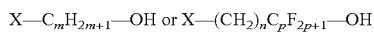
X—$C_mH_{2m+1}$—OH or X—$(CH_2)_nC_pF_{2p+1}$—OH in the presence of esterification catalyst or by reacting acid chloride corresponding to the aforementioned carboxylic acid with

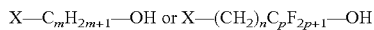
X—$C_mH_{2m+1}$—OH or X—$(CH_2)_nC_pF_{2p+1}$—OH in the presence of tertiary amine.

Next, the polyimide composition according to the present invention includes a polyimide with a reactive group which has photoreactivity and thermoreactivity.

Specifically, the polyimide composition of the present invention includes a polyimide comprising at least one of an acid dianhydride component having a reactive group through an alkylene group or fluoroalkylene group and a diamine component having a reactive group through an alkylene group or fluoroalkylene group in its molecule. The aforementioned reactive group may be selected from the group consisting of: monovalent organic groups derived from cinnamic acid, chalcone, furylacryloyl, benzalacetophenone, stilbene, coumarin, and pyrone; allyl; propargyl; ethinyl; $CH_2$=CH—; and $CH_2$=$C(CH_3)$—. The alkylene group may be C2 to C30, and the fluoroalkylene group may be C4 to C30. The polyimide having a reactive group such as cinnamic acid, chalcone, furylacryloyl, benzalacetophenone, stilbene, coumarin, pyrone, allyl, propargyl, and ethinyl can be prepared by reacting a diamine and/or acid dianhydride having the aforementioned reactive group in an organic polar solvent to prepare polyamic acid and then by reacting the polyamic acid with tetrafluoro acetic acid anhydride or dicyclohexane carbodiimide in the presence of tertiary amine.

Likewise, the polyimide having a reactive group such as cinnamic acid, chalcone, furylacryloyl, benzalacetophenone, stilbene, coumarin, pyrone, allyl, propargyl, and ethinyl can be prepared by reacting polyamic acid with acid anhydride such as acetic anhydride in the presence of tertiary amine such as pyridine, picoline, and isoquinoline.

A weight-average molecular weight of the polyamic acid is preferably 5,000 to 1,000,000. It is not preferable to use the polyamic acid having an average molecular weight of less than 5,000, because polyimide to be produced therefrom has low molecular weight so that such polyimide is too brittle to use as photoreactive resin. Also, it is not preferable to use the polyamic acid having an average molecular weight of more than 1,000,000, because a viscosity of polyamic acid vanish is too high to handle.

Various organic additives, inorganic fillers, or reinforcements can be mixed with the polyimide of the present invention.

Example of the organic polar solvents to be used to produce the aforementioned polyamic acid include sulfoxide solvents such as dimethyl sulfoxide and diethyl sulfoxide; formamide solvents such as N,N-dimethylformamide and N,N-diethylformamide; acetamide solvents such as N,N-dimethylacetamide and N,N-diethylacetamide; pyrrolidone solvents such as N-methyl-2-pyrrolidone and N-vinyl-2-pyrrolidone; hexamethylphosphoramide; and y-butyrolactone. These solvents are can be used alone or in combination thereof, or can be used by mixing aromatic hydrocarbon solvents such as xylene and toluene.

The acid dianhydride to be used in this polyimide is not particularly limited to the acid dianhydride represented by the aforementioned general formula (1). Examples of acid dianhydrides include: aliphatic or alicyclic tetracarboxylic dianhydride such as butane tetracarboxylic dianhydride, 1,2,3,4-cyclobutane tetracarboxylic dianhydride, 1,3-dimethyl-1,2,3,4-cyclobutane tetracarboxylic dianhydride, 1,2,3,4-cyclopetane tetracarboxylic dianhydride, 2,3,5-tricarboxycyclopentylacetic dianhydride, 3,5,6-tricarboxy norbornane-2-acetic dianhydride, 2,3,4,5-tetrahydrofuran tetracarboxylic dianhydride, 5-(2,5-dioxysotetrahydrofural)-3-methyl-3-cyclohexene-1,2-dicarboxylic dianhydride, bicyclo[2,2,2]-octo-7-ene-2,3,5,6-tetracarboxylic dianhydride; aromatic tetracarboxylic dianhydride such as pyromellitic dianhydride, 3,3',4,4'-benzophenone tetracarboxylic dianhydride, 3,3',4,4'-biphenylsulfone tetracarboxylic dianhydride, 1,4,5,8-naphtalene tetracarboxylic dianhydride, 2,3,6,7-naphtalene tetracarboxylic dianhydride, 3,3',4,4'-biphenyl ether tetracarboxylic dianhydride, 3,3',4,4'-dimethyldiphenylsilane tetracarboxylic dianhydride, 3,3',4,4'-tetraphenylsilane tetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfonic dianhydride, 4,4'-bis(3,4-dicarboxyphenoxy)diphenylpropane dianhydride, 3,3',4,4'-perfluoro isopropylidene diphthalic dianhydride, 3,3',4,4'-biphenyltetracarboxylic dianhydride, bis(phthalic acid) phenylphosphine oxide dianhydride, p-phenylene-bis(triphenyl phthalic acid)dianhydride, m-phenylene-bis(triphenyl phthalic acid)dianhydride, bis(triphenyl phthalic acid)-4,4'-diphenyl ether dianhydride, bis(triphenyl phthalic acid)-diphenylmethane dianhydride; and aliphatic tetracarboxylic dianhydride having an aromatic ring such as 1,3,3a,4,5,9b-hexahydro-2,5-dioxo-3-furanyl-naphtho[1,2-c]furan-1,3-dion, 1,3,3a,4,5,9b-hexahydro-5methyl-5-(tetrahydro-2,5-dioxo-3-furany)-naphtho[1,2c]furan-1,3-dion,1,3,3a,4,5,9b-hexahydro-8-methyl-5-(tetrahydro-2,5-dioxo-3-furanyl)-naphtho[1,2-c]furan-1,3-dion, a compound represented by the general formula (C):

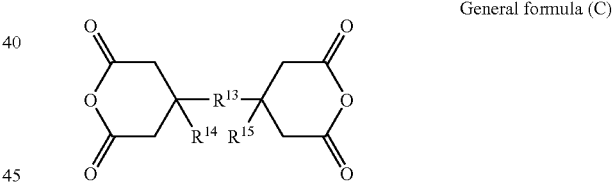

General formula (C)

(wherein $R^{13}$ represents a divalent organic group having an aromatic group, and $R^{14}$ and $R^{15}$ each represent a hydrogen atom or an alkyl group, independently); and a compound represented by the general formula (D):

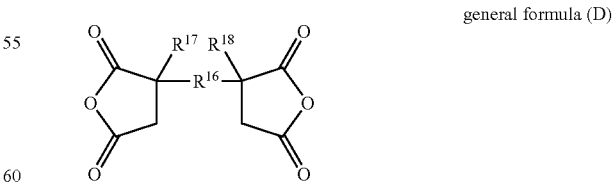

general formula (D)

(wherein $R^{16}$ represents a divalent organic group having an aromatic ring, and $R^{17}$ and $R^{18}$ each represent a hydrogen atom or an alkyl group, independently). These tetracarboxylic dianhydrides can be used alone or in combination of two or more.

Not only the diamines represented by the general formulas (2) and (3) but various diamines can also be used. Although these diamines are not particularly limited, examples of diamines include: aromatic diamines such as p-phenylenediamine, m-phenylenediamine, 4,4'-diaminodiphenylmethane, 4,4'-diaminodiphenylethane, 4,4'-diaminodiphenyl ether, 4,4'-diaminodiphenylsulfide, 4,4'-diaminodiphenylsulfone, 1,5-diaminonaphthalene, 3,3'-dimethyl-4,4'-diaminobiphenyl, 5-amino-1-(4'-aminophenyl)-1,3,3-trimethylindane, 6-amino-1-(4'-aminophenyl)-1,3,3-trimethylindane, 4,4'-diaminobenzanilide, 3,5-diamino-3'-trifluoromethylbenzanilide, 3,5-diamino-4'-trifluoromethylbenzanilide, 3,4'-diaminodiphenyl ether, 2,7-diaminofluorene, 2,2-bis(4-aminophenyl)hexafluoropropane, 4,4'-methylene-bis(2-chloroaniline), 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-diamino-2,2'-bis(trifluoromethyl)biphenyl, 2,2-bis[4-(4-aminophenoxy)phenyl]propane, 2,2-bis[4-(4-aminophenoxy)phenyl]hexafluoropropane, 1,4-bis(4-aminophenoxy)benzene, 4,4'-bis(4-aminophenoxy)-biphenyl, 1,3'-bis(4-aminophenoxy)benzene, 9,9-bis(4-aminophenyl)fluorene, 4,4'-(p-phenylene isopropylidene)bisaniline, 4,4'-(m-phenylene isopropylidene)bisaniline, 2,2'-bis[4-(4-amino-2-trifluoromethylphenoxy)phenyl]hexafluoropropane, 4,4'-bis[4-(4-amino-2-trifluoromethyl)phenoxy]-octafluorobiphenyl; aromatic diamines having two amino groups bonded to an aromatic ring and a hetero atom except nitrogen atom of the amino group such as diamino tetraphenyl thiophene; aliphatic diamines and alicyclic diamines such as 1,1metaxylylenediamine, 1,3-propane diamine, tetramethylene diamine, pentamethylene diamine, octamethylene diamine, nonamethylene diamine, 4,4-diaminoheptamethylene diamine, 1,4-diaminocyclohexane, isophorone diamine, tetrahydrodicyclopentadienylene diamine, hexahydro-4,7-methanoindanylene dimethylenediamine, tricyclo[6,2,1,0$^{2,7}$] undecylene dimethyldiamine, and 4,4'-methylenebis(cyclohexylamine); mono-substituted phenylenediamines such as following general formula:

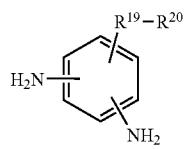

(wherein $R^{19}$ represents a divalent organic group selected from the group consisting of: —O—, —COO—, —OCO—, —CONH, and —CO—, and $R^{20}$ represents a monovalent organic group having a steroid skeleton); and compounds represented by the general formula:

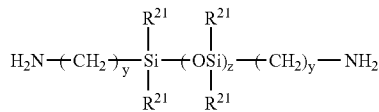

(wherein $R^{21}$ represents a hydrocarbon group having a carbon number of 1 to 12, y is an integer of 1 to 3, and z is an integer of 1 to 20.) These diamine can be used alone or in combination.

Next, a method of synthesizing polyamic acid will be described. First, in an inert atmosphere such as argon and nitrogen, diamine and acid anhydride are dissolved or diffused in an organic solvent. Although any aforementioned diamine and acid dianhydride can be used, one or more of the acid dianhydride having a reactive group as represented by the general formula (1) and the diamine having a reactive group as represented by the general formula (2) or (3) must be used so as to obtain the polyimide having a reactive group according to the present invention.

Where the diamine and the acid dianhydride have a different mole ratio, a diamine compound represented by the general formula:

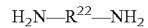

(wherein $R^{22}$ represents a divalent organic group) is dissolved in an organic solvent and diffused in a slurry state or in a solid state and then added to the aforementioned polyamic acid solution. After that, acid dianhydride represented by the following general formula:

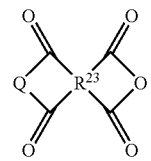

(wherein $R^{23}$ is a tetravalent organic group) is added to the above-obtained solution and thus a polyamic acid copolymer solution is obtained. Any polyamic acid copolymer solution can be prepared by controlling the mole ratio of acid dianhydride component to diamine component.

The adding order of monomers is as follows. A diamine component may be first added to an organic polar solvent, and then an acid dianhydride component may be added to prepare a polyamic acid copolymer solution. Alternatively, one of the diamine components is first added to an organic polar solvent, and then one of the acid dianhydride component is added. After that another diamine component is added and then another acid dianhydride component is added to prepare a polyamic acid copolymer solution. Alternatively, a diamine component is added to an organic polar solvent in advance and then various kinds of acid dianhydride compounds are added at the same time to prepare a polyamic acid copolymer solution. Acid dianhydride and diamine components can be added in reverse order. Substantially the same result can be achieved.

The adding order of monomers may vary as long as the acid dianhydride component and/or diamine component has/have reactive groups. The preferable reaction temperature ranges from −20° C. to 60° C., and the preferable reaction time ranges from 30 minutes to 24 hours.

A desired polyimide can be prepared by reacting the thus-obtained polyamic acid copolymer with acid anhydride such as acetic anhydride in the presence of tertiary amine such as pyridine, picoline, and isoquinoline.

Polyamide can be also prepared by reacting the diamine of the present invention with a condensation agent and dicarboxylic acid or with dicarboxy chloride.

Various organic additives, organic fillers, or reinforcing agents can be mixed with thus-obtained polyimide having a reactive group according to the present invention.

It is preferable that a photoreaction initiator is mixed with the polyimide composition having a reactive group according to the present invention so as to provide photosensitivity to the polyimide.

An example of compound that generates radicals by long wavelength light such as g ray and that is used as a photoreaction initiator is an acylphosphine oxide compound represented by the following general formulas (α,β):

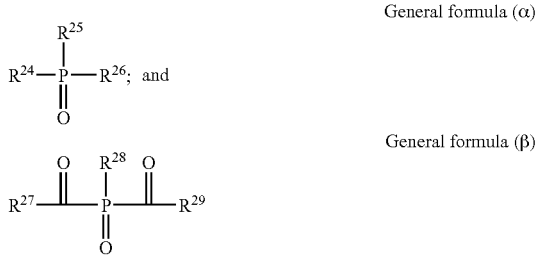

(wherein $R^{24}$, $R^{27}$, and $R^{29}$ represent $C_6H_5$—, $C_6H_4(CH_3)$—, $C_6H_2(CH_3)_3$—, $(CH_3)_3C$—, or $C_6H_3Cl_2$—; $R^{25}$, $R^{26}$, and $R^{28}$ represent $C_6H_5$—, methoxy, ethoxy, $C_6H_4(CH_3)$—, or $C_6H_2(CH_3)_3$—. In this case, the generated radicals are reacted with a reactive group (such as vinyl, acroyl, methacroyl and allyl) to promote cross-links.

Particularly, the acylphosphine oxide represented by the general formula (β) is preferable because it generates four radicals by a cleavage. (In the general formula (a), two radicals are generated.

As a radical initiator, various peroxides can be used in combination with any following sensitizer. Particularly preferable sensitizer is 3,3', 4,4'-tetra(t-butylperoxy carbonyl) benzophenone.

In order to achieve a practicable degree of photosensitivity, a polyimide composition of the present invention can contain a sensitizer. Preferable examples of the sensitizer include: Michler ketone, bis-4,4'-diethylamino benzophenone, benzophenone, camphorquinone, benzil, 4,4'-dimethylaminobenzil, 3,5-bis(diethylamino benzylidene)-N-methyl-4-piperidone, 3,5-bis(dimethylamino benzylidene)-N-methyl-4-piperidone, 3,5-bis(diethylamino benzylidene)-N-ethyl-4-piperidone, 3,3'-carbonylbis(7-diethylamino)coumarin, riboflavin tetrabutyrate, 2-methyl-1-[4-(methylthio)phenyl] 2-morpholinopropane-1-one, 2,4-dimethylthioxanthone, 2,4-diethylthioxanthone, 2,4-diisopropylthioxanthone, 3,5-dimethylthioxanthone, 3,5-diisopropylthioxanthone, 1-phenyl-2-(ethoxycarbonyl)oxyiminopropane-1-one, benzoin ether, benzoin isopropyl ether, benzanthrone, 5-nitroacenaphthene, 2-nitrofluorene, anthrone, 1,2-benzanthraquinone, 1-phenyl-5mercapto-1H-tetrazole, thioxanthen-9-one, 10-thioxanthenone, 3-acetylindole, 2,6-di(p-dimethylaminobenzal)-4-carboxy cyclohexanone, 2,6-di(p-dimethylaminobenzal)-4-hydroxy cyclohexanone, 2,6-di(p-diethylaminobenzal)-4-carboxy cyclohexanone, 2,6-di(p-diethylaminobenzal)-4-hydroxy cyclohexanone, 4,6-dimethyl-7-ethylaminocoumarin, 7-diethylamino-4-methylcoumarin, 7-diethylamino-3-(1methylbenzimidazolyl)coumarin, 3-(2-benzoimidazolyl)-7-diethylamino coumarin, 3-(2-benzothiazolyl)-7-diethylamino coumarin, 2-(p-dimethylamino styryl)benzoxazole, 2-(p-dimethylamino styryl)quinoline, 2-(p-dimethylamino styryl)benzothiazole, and 2-(p-dimethylamino styryl)-3,3-dimethyl-3H-indole. However, the sensitizer is not limited to the above.

It is more preferable that 0.1 to 50 parts by weight of sensitizer is contained in 100 parts by weight of the polyimide of the present invention. If the content of the sensitizer deviates from the above range, desired sensitizing effects cannot be produced, which exerts an undesirable influence on developing properties. As a sensitizer, one or more kinds of compounds may be mixed.

In order to achieve a practicable degree of photosensitivity, a polyimide composition of the present invention can contain a photopolymerization assistant. Preferable examples of the photopolymerization assistant include: 4-diethylaminoethylbenzoate, 4-dimethylaminoethylbenzoate, 4-diethylaminopropylbenzoate, 4-dimethylaminopropylbenzoate, 4-dimethylamino isoamylbenzoate, N-phenylglycine, N-methyl-N-phenylglycine, N-(4cyanophenyl)glycine, 4-dimethylaminobenzonitrile, ethylene glycol dithioglycolate, ethylene glycol di(3-mercapto propionate), trimethylolpropane thioglycolate, trimethylolpropane tri(3-mercapto propionate), pentaerythritol tetrathioglycolate, pentaerythritol tetra(3mercapto propionate), trimethylolethane trithioglycolate, trimethylolpropane trithioglycolate, trimethylolethane tri(3mercapto propionate), dipentaerythritol hexa(3-mercapto propionate), thioglycolic acid, α-mercapto propionic acid, t-butylperoxybenzoate, t-butylperoxymethoxybenzoate, t-butylperoxynitrobenzoate, t-butylperoxyethylbenzoate, phenyl isopropylperoxybenzoate, di-t-butylperoxyisophthalate, tri-t-butyltriperoxy trimellitate, tri-t-butyltriperoxy trimellitate, tetra-t-butyltetraperoxy pyromellitate, 2,5-dimethyl-2,5-di(benzoylperoxy)hexane, 3,3', 4,4'-tetra(t-butylperoxy carbonyl) benzophenone, 3,3,4,4'-tetra(t-amylperoxycarbonyl)benzophenone, 3,3', 4,4'-tetra(t-hexylperoxycarbonyl)benzophenone, 2,6-di(p-azidobenzal)-4hydroxycyclohexanone, 2,6-di(p-azidobenzal)-4carboxycyclohexanone, 2,6-di(p-azidobenzal)-4methoxycyclohexanone, 2,6-di(p-azidobenzal)-4hydroxymethylcyclohexanone, 3,5-di(p-azidobenzal)-1-methyl-4piperidone, 3,5-di(p-azidobenzal)-4-piperidone, 3,5-di(p-azidobenzal)-N-acetyl-4-piperidone, 3,5-di(p-azidobenzal)-N-methoxycarbonyl-4-piperidone, 2,6-di(p-azidobenzal)-4hydroxycyclohexanone, 2,6-di(m-azidobenzal)-4carboxycyclohexanone, 2,6-di(m-azidobenzal)-4methoxycyclohexanone, 2,6-di(m-azidobenzal)-4hydroxymethylcyclohexanone, 3,5-di(m-azidobenzal)-N-methyl-4piperidone, 3,5-di(m-azidobenzal)-4-piperidone, 3,5-di(m-azidobenzal)-N-acetyl-4-piperidone, 3,5-di(m-azidobenzal)-N-methoxycarbonyl-4-piperidone, 2,6-di(p-azidocinnamylidene)-4hydroxycyclohexanone, 2,6-di(p-azidocinnamylidene)-4carboxycyclohexanone, 2,6-di(p-azidocinnamylidene)-4cyclohexanone, 3,5-di(p-azidocinnamylidene)-N-methyl-4piperidone, 4,4'-diazidochalcone, 3,3'-diazidochalcone, 3,4'-diazidochalcone, 4,3'-diazidochalcone, 1,3-diphenyl-1,2,3-propanetrione-2-(o-acetyl)oxime, 1,3-diphenyl-1,2,3propanetrione-2-(o-n-propylcarbonyl)oxime, 1,3-diphenyl-1,2,3-propanetrione-2-methoxycarbonyl)oxime, 1,3-diphenyl-1,2,3-propanetrione-2-(o-ethoxycarbonyl)oxime, 1,3-diphenyl-1,2,3-propanetrione-2-(o-benzoyl)oxime, 1,3-diphenyl-1,2,3propanetrione-2-(o-phenyloxycarbonyl) oxime, 1,3-bis(p-methylphenyl)-1,2,3-propanetrione-2-(o-benzoyl)oxime, 1,3bis(p-methoxyphenyl)-1, 2,3-propanetrione-2-(o-ethoxycarbonyl)oxime, and 1-(p-methoxyphenyl)-3-(p-nitrophenyl)-1,2,3-propanetrione-2-(o-phenyloxycarbonyl)oxime. However, the photopolymerization assistant is not limited to the above. As other assistant, trialkylamines such as triethylamine, tributylamine, and triethanol can be also used.

Preferably, 0.1 to 50 parts by weight of photopolymerization assistant is contained in 100 parts by weight of polyimide, and more preferably 0.3 to 20 parts by weight is contained. If the content of the photopolymerization assistant deviates from the above range, desired sensitizing effects cannot be produced, which exerts an undesirable influence on developing properties. In the present invention, one or more kinds of compounds may be mixed as a photopolymerization assitant.

EXAMPLES

The present invention will be more concretely described by referring to the examples which follow. These examples should not be construed to limit the invention in any way.

In the following Examples, the measurements were carried out as follows:

(IR): Transmitted light of a pellet produced by mixing a sample material with KBr powders was measured using FT-IR System 2000 available from PerkinElmer Instruments, Inc.

($^1$H-NHR): A sample material was dissolved in a mixture of dimethyl sulfoxide deuteride and chloroform deuteride to prepare about 4% sample solution, and then it was subjected to measurement using PMX60si NMR spectrometer available from JAPAN ELECTRON OPTICS LABORATORY CO., LTD. in accordance with a tetramethylsilane standard.

(Weight-average molecular weight): Weight-average molecular weight was determined by gel permeation chromatography (GPC available from Waters Corporation) under the following conditions:

(Column: two columns KD-806M available from Shodex, 60° C.

Detector: $R^1$ (Refractive Index)
Flow rate: 1 mL per minute
Developer: DMF (0.03M of lithium bromide and 0.03M of phosphoric acid)
Concentration of sample solution: 0.2 wt %
Injection amount: 20 μl
Reference material: polyethylene oxide)

The following Example 1 is an example of synthesizing acid dianhydride having a reactive group according to the present invention.

Example 1

(1-1) Synthesis of 12-bromododecane-1-(4-fluorocinnamate):

4.6 g (25 mmol) of 4-fluorocinnamic acid chloride and 50 mL of methyl ethyl ketone were placed in a reaction vessel. Then a mixture prepared by dissolving 5.0 g (18.9 mmol) of bromododecanol and 3.0 g (30 mmol) of triethylamine in 50 mL of methyl ethyl ketone was added dropwise in the reaction vessel and refluxed with stirring under a nitrogen atmosphere. The resulting quaternary salt was filtered out. After being concentrated by drying, the filtrate was recrystallized with methanol. Thus 7.4 g (17.9 mmol) of 12-bromododecane-1-(4fluorocinnamate) was prepared. The yield was 95%.

$^1$H-NMR (solvent: CDCl$_3$): δ7.85 to 6.93 (m, Ph-H, 4H), 6.50 (s, CH=CH, 1H), 6.25 (s, CH=CH, 1H), 4.20 (t, CH, 2H), 3.40 (t, CH, 2H), 1.90 to 0.9 (m, CH, 20H)

(1-2) Synthesis of 12-(4-fluorocinnamic acid)-dodecane-1-(2,5-dihydroxydibenzoate):

7.33 g (17.5 mmol) of 12-bromododecane-1-(4fluorocinnamate), 5.72 g (20 mmol) of cesium salt of 2,5-dihydroxybenzoic acid, and 50 mL of dimethylformamide were placed in a reaction vessel and heated with stirring at 100° C. under a nitrogen atmosphere. The resulting CsBr was filtered out and the filtrate was poured into ice water to precipitate a solid. The solid was separated from the solution and then dried.

Thus 7.66 g (15.7 mmol) of 12-(4-fluorocinnamic acid)-dodecane-1-(2,5-dihydroxydibenzoate) was prepared. The yield was 90%.

$^1$H-NMR (solvent: CDCl$_3$): δ7.85 to 6.70 (m, Ph-H.OH, 9H), 6.50 (s, CH=CH, 1H), 6.25 (s, CH=CH, 1H), 4.20 (t, CH, 4H), 1.90 to 0.9 (m, CH, 20H)

(1-3) Synthesis of the following acid dianhydride

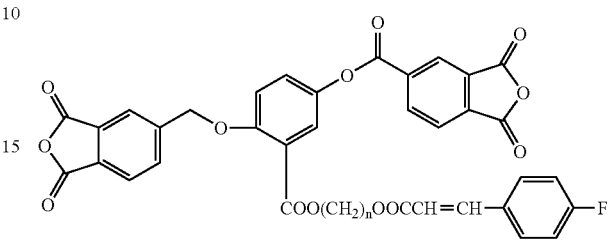

7.37 g (35 mmol) of trimellitic chloride and 100 mL of toluene were placed in a reaction vessel. Then 7.30 g (15 mmol) of 12-(4-fluorocinnamic acid)-dodecane-1-(2,5-dihydroxydibenzoate) and 3.16 g (40 mmol) of pyridine were dissolved in 50 g of toluene, and added dropwise to the reaction vessel. After completion of dropping, the solution was refluxed with stirring for 2 hours (under a nitrogen atmosphere).

After the reaction, the reaction solution was filtered, and the filtrate was concentrated to precipitate a solid. The solid was then recrystallized with acetic anhydride. Thus, 8.35 g (10 mmol) of the aforementioned acid dianhydride was prepared.

$^1$H-NMR (solvent: CDCl$_3$): δ7.85 to 6.70 (m, Ph-H, 13H), 6.50 (s, CH=CH, 1H), 6.25 (s, CH=CH, 1H), 4.20 (t, CH, 4H), 1.90 to 0.9 (m, CH, 20H)

The following Examples 2 to 6 each show an example of synthesis of diamine having a reactive group according to the preset invention.

Example 2

(2-1) Synthesis of 1-dodecanol-12-(4-fluorocinnamate)

7.23 g (25 mmol) of cesium salt of cinnamic acid, 5.0 g (18.9 mmol) of 12-bromododecanol, and 50 mL of dimethylformamide (hereinafter referred to as "DMF") were placed in a reaction vessel, and heated with stirring at 100° C. for two hours (under a nitrogen atmosphere). After the reaction solution was filtered, the filtrate was poured into water for precipitation and a white solid was filtered out. Thus 6.26 g (18.3 mmol) of 1-dodecanol-12-(4-fluorocinnamate) was prepared. (The yield was 97%)

$^1$H-NMR (solvent: CDCl$_3$): δ7.85 to 6.93 (m, Ph-H, 4H), 6.50 (s, CH=CH, 1H), 6.26 (s, CH=CH, 1H), 4.20 (t, CH, 2H), 3.76 (t, CH, 2H), 1.90 to 0.8 (m, CH, 20H), 1.8 (s, OH, 1H)

(2-2) Synthesis of 12-(4-fluorocinnamic acid)-dodecane-1-(3,5-dinitrobenzoate):

6.15 g (18 mmol) of 1-dodecanol-12-(4-fluorocinnamate), 2.5 g (25 mmol) of triethyl amine, and 60 mL of methyl ethyl ketone were placed in a reaction vessel. Then 4.61 g (20 mmol) of 3,5-dinitrobenzoyl chloride was dissolved in 50 mL of methyl ethyl ketone, and added dropwise to the reaction vessel (under a nitrogen atmosphere). After the reaction solution was filtered, the filtrate was concentrated and recrystallized with methanol. Thus, 8.67 g (16.2 mmol) of 12-(4- fluorocinnamic acid)-dodecane-1-(3,5-dinitrobenzoate) was prepared. (The yield was 90%.)

$^1$H-NMR (solvent: CDCl$_3$): δ9.20 (s, Ph-H, 1H), 9.10 (s, Ph-H, 2H), 7.75 to 6.85 (m, Ph-H, 4H), 6.43 (s, CH=CH, 1H), 6.15 (s, CH=CH, 1H), 4.43 (t, CH, 2H), 4.16 (t, OH, 2H), 2.1 to 1.1 (m, CH, 20H)

(2-3) Synthesis of 12-(4-fluorocinnamic acid)-dodecane-1-(3,5-diaminobenzoate)

8.57 g (16 mol) of 12-(4-fluorocinnamic acid)-dodecane-1-(3,5-dinitrobenzoate), 3 g of 5% Pt-carbon black (5 wt % of platinum supported on carbon black), and 100 mL of dioxane were reacted in a hydrogeneration apparatus at 60° C. until hydrogen absorption was completed (hydrogen absorption of about 2.3 litter). The reaction mixture was filtered to remove a catalyst and then concentrated. Thus, 7.60 g (16 mmol) of 12-(4-fluorocinnamic acid)-dodecane-1-(3,5-diaminobenzoate) was prepared. (The yield was 100%)

$^1$H-NMR (solvent: CDCl$_3$): δ7.70 to 6.80 (m, Ph-H, 4H), 6.50 (w, Ph-H, 2H), 6.40 (s, CH=CH, 1H), 6.15 (s, CH=CH, Ph-H, 2H), 5.4 (s, NH, 4H), 4.40 (t, CH, 2H), 4.10 (t, CH, 2H), 2.10 to 0.9 (m, CH, 20H)

Example 3

(3-1) 12-(3,5-dinitrobenzyloxy)-dodecanol 5.9 g (18.9 mmol) of 12-bromododecanol, 1.06 g (10 mmol) of sodium carbonate, 4.92 g of (25 mmol) of 3,5-dinitrobenzyl alcohol were dissolved in 50 mL of DMF and heated with stirring at 100° C. for 12 hours (under a nitrogen atmosphere). The reaction solution was poured into ice water to precipitate a solid, and the solid was recrystallized with methanol. Thus, 5.73 g (15 mmol) of 12-(3,5-dinitrobenzyloxy)-dodecanol was prepared. (The yield was 79%.)

$^1$H-NMR (solvent: CDCl$_3$): δ8.70 (s, Ph-H, 4H), 8.50 (s, Ph-H, 1H), 4.9 (s, CH, 2H), 4.00 (t, CH, 2H), 3.40 (t, CH, 2H), 1.90 to 0.9 (m, CH, 20H), 1.8 (s, OH, 1H)

(3-2) 12-(3,5-dinitrobenzyloxy)-dodecane-1-(furylacrylate)

5.73 g (15 mmol) of 12-(3,5-dinitrobenzyloxy)-dodecanol, 2.0 g (20 mmol) of triethylamine, and 100 mL of methyl ethyl ketone were placed in a reaction vessel. Then 3.13 g (20 mmol) of furylacryloylchloride was dissolved in 50 mL of methyl ethyl ketone, and added dropwise in the reaction vessel (under a nitrogen atmosphere). After the reaction solution was filtered, the filtrate was concentrated and recrystallized with methanol. Thus 6.41 g (12.75 mmol) of 12-(3,5-dinitrobenzyloxy)-dodecane-1-(furylacrylate) was prepared.

(The Yield was 85%.)

$^1$H-NMR (solvent: CDCl$_3$): δ8.70 (s, Ph-H, 1H), 8.50 (s, Ph-H, 2H), 7.6 to 6.3. (m, furan ring, 3H), 6.35 (s, CH=CH, 1H), 6.08 (s, CH=CH, 1H), 4.9 (s, CH, 2H), 4.20 (t, CH, 2H), 4.00 (t, CH, 2H), 1.90 to 0.9 (m, CH, 20H)

(3-3) Synthesis of 12-(3,5-diaminobenzyloxy)-dodecane-1-(furylacrylate)

6.41 g (12.75 mmol) of 12-(3,5-dinitrobenzyloxy)dodecane-1-(furylacrylate), 3 g of 5% Pt-2% Fe-carbon powders (5 wt % of platinum and 2% of iron supported on carbon black) and 100 mL of dioxane were reacted in a hydrogeneration apparatus at 60° C. until hydrogen absorption was completed (hydrogen absorption of about 1.8 litter). The reaction mixture was filtered to remove a catalyst and then concentrated. Thus, 5.64 g (12.75 mol) of 12-(3,5-diaminobenzyloxy)-dodecane-1-(furylacrylate) was prepared.

(The Yield was 100%)

$^1$H-NMR (solvent: CDCl$_3$): δ7.6 to 6.3 (m, furan ring, 3H), 6.35 (s, CH=CH, 1H), 6.08 (s, CH=CH, 1H), 5.90 (s, Ph-H, 1H), 5.80 (s, Ph-H, 2H), 4.9 (s, CH, 2H), 4.20 (t, CH, 2H), 4.00 (t, CH, 2H), 1.90 to 0.9 (m, CH, 20H)

Example 4

(4-1) Synthesis of 1,1-{4,4'-bis[2-carboxycesium (phenyl-t-butoxyurethane)]}methane:

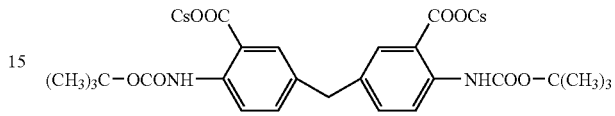

42.94 g (0.15 mmol) of 1,1-bis(4-amino-3carboxyphenyl) methane(MBAA), 48.87 g (0.15 mol) of cesium carbonate, 100 mL of dioxane, and 100 mL of water were reacted with stirring at room temperature for 3 hours. After the completion of the reaction, the reaction solution was concentrated and dried. Thus, 112.5 g of 1,1-(4,4'-bis[2carboxycesium (phenyl-t-butoxyurethane)])methane was prepared. IR (KBr): 2979 (CH$_3$), 1697 cm$^{-1}$ (C=O), $^1$H-NMR: δ9.75 (s, Ph-OH, 2H), 7.60 (s, NHCO, 2H), 7.70 to 6.80 (m, Ph-H, 6H), 1.47 (s, CH$_3$, 18H)

(4-2) Synthesis of 1,1-{4,4'-bis[2-(1-hexadecane carboxylate) phenyl-t-butoxyuretane]}methane

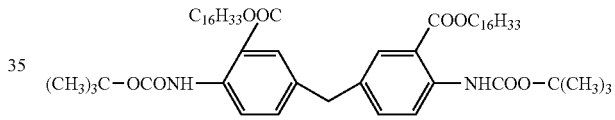

37.52 g (50 mmol) of 1,1-{4,4'-bis[2carboxycesium(phenyl-t-butoxyurethane)])methane, 30.53 g (100 mmol) of 1-bromohexadecane, and 150 mL of dimethylformamide were placed in a reaction vessel and stirred at 100° C. for 3 hours under a nitrogen atmosphere.

The reaction solution was filtered to remove CsBr, and then poured into 1000 mL of ice water for precipitation. The precipitate was separated from the solution and dried. Thus, 1,1-(4,4'-bis[2-(1-hexadecane carboxylate) phenyl-tbutoxyuretane]}methane was prepared. IR (KBr): 3365 (NH), 2982 (CH$_3$), 1746 (C=O), 1714 cm$^{-1}$ (C=O)

(4-3) Synthesis of 1,1-(4,4'-bis[4-amino-2-(1-hexadecane carboxylate)phenyl]}methane:

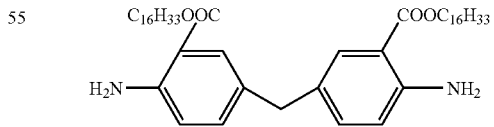

42.09 g (45 mmol) of 1,1-{4,4'-bis[2-(1-hexadecane caroxylate)phenyl-t-butoxyuretane]}methane was added to 100 g of trifluoroacetic acid and stirred at room temperature for an hour. The solution was poured into 1000 mL of water and neutralized with sodium carbonate. The precipitate was washed with filtrate water and dried to prepare 29.7 g of solid. The solid was then recrystallized with isopropyl alcohol.

Thus, 22.8 g of 1,1-{4,4'-bis[4-amino-2-(1hexadecane carboxylate)phenyl]}methane was prepared. (The yield was 85.8%.)

IR (KBr): 3411 (NH), 3329 (NH), 1718 cm$^{-1}$ (C=O), $^1$H-NMR: δ7.70 to 6.85 (m, Ph-H, 6H), 6.53 (s, NH$_2$, 4H), 4.20 (t, CH, 4H), 3.70 (s, CH, 2H), 1.90 to 0.9 (m, CH, 62H)

Example 5

(5-1) Synthesis of 1,1-{4,4'-bis[4-amino-3-(12-(4-fluorocinnamicaciddodecane carboxylate)phenyl)]methane:

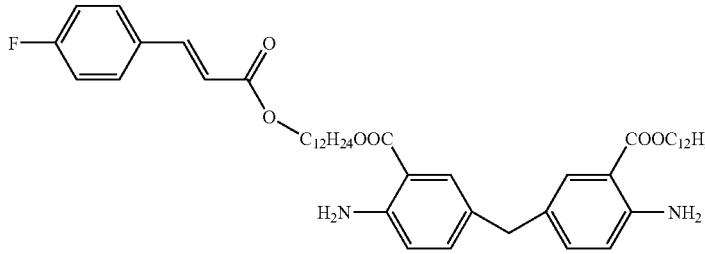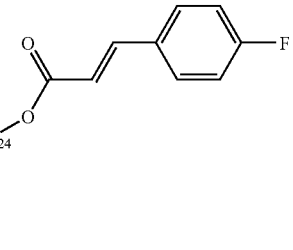

37.52 g (50 mmol) of 1,1-{4,4'-bis[2carboxycesium(phenyl-t-butoxyurethane)]}methane prepared in Example 4, 41.3 g (100 mmol) of 12-bromododecane-1-(4fluorocinnamate) prepared in Example 1, and 150 mL of dimethylformamide were placed in a reaction vessel and stirred at 100° C. for 3 hours under a nitrogen atmosphere. The reaction solution was filtered to remove CsBr, and then poured into 1000 mL of ice water for precipitation. The precipitate was separated from the solution and dried, and a white solid was obtained. The solid was added to 100 g of trifluoroacetic acid, and stirred at room temperature for an hour. The solution was poured into 1000 mL of water and neutralized with sodium carbonate. The precipitate was washed with filtrate water and dried to prepare 32 g of solid. The solid was then recrystallized with isopropyl alcohol. Thus, 27.7 g of 1,1-{4,4'-bis[4-amino-3-(12-(4-fluorocinnamicaciddodecane carboxylate)phenyl)]}methane was prepared.

IR (KBr): 3411 (NH), 3329 (NH), 1718 cm$^{-1}$ (C=O), $^1$H-NMR: δ7.85 to 6.90 (m, Ph-H, 14H), 6.83 (s, CH=CH, 2H), 6.53 (s, CH=CH, 2H), 6.40 (s, NH$_2$, 4H), 4.20 (t, CH, 8H), 3.70 (s, CH, 2H), 1.90 to 0.9 (m, CH, 40H)

Example 6

(6-1) Synthesis of 1,1-{4,4'-bis[4-amino-3-(12-(4fluorocinnamicaciddodecane carboxylate)phenyl)]}methane:

15 g (20 mmol) of 1,1-(4,4'-bis[2-carboxycesium(phenyl-t-butoxyurethane)]}methane prepared in Example 4, 10.58 g (40 mmol) of 12-bromododecanol, and 50 mL of dimethylformamide were placed in a reaction vessel and stirred at 100° C. for 3 hours under a nitrogen atmosphere.

The reaction solution was filtered to remove CsBr, and then poured into 1000 mL of ice water for precipitation. The precipitate was separated from the solution and dried, and 17.00 g of a white solid was obtained.

17.00 g of the solid, 4.0 g (40 mmol) of triethylamine, and 50 mL of methyl ethyl ketone were placed in a reaction vessel, and then a solution prepared by dissolving 7.36 g (40 mmol) of 4-fluorocinnamic acid chloride in 50 mL of methyl ethyl ketone was added dropwise to the reaction vessel and refluxed with stirring under a nitrogen atmosphere. The resulting quaternary salt was filtered out. After being concentrated by drying, a white solid was obtained.

The solid was added to 100 g of trifluoroacetic acid, and stirred at room temperature for an hour. The solution was poured into 1000 mL of water and neutralized with sodium carbonate. The precipitate was washed with filtrate water and dried, and then 32 g of solid was obtained. The solid was then recrystallized with isopropyl alcohol. Thus, 9.5 g of 1,1-{4,4'-bis[4-amino-3-(12-(4-fluorocinnamicacid-dodecane carboxylate)phenyl)]}methane was prepared.

IR and $^1$H-NMR were the same as those in the Example 5.

The following Examples 7 to 12 each show an example of synthesis of polyimide having a reactive group according to the preset invention.

Example 7

4.30 g (10 mmol) of [4-(3-aminophenoxy)phenyl]sulfone and 50 g of dimethylformamide (hereinafter referred to as "DMF") were placed in a 2000 mL separable flask equipped with a stirrer. Then 8.35 g (10 mmol) of acid dianhydride prepared in Example 1 was added at a dash with vigorous stirring, and continuously stirred for 30 minutes to obtain polyamic acid solution. 10 g of acetic anhydride, 5 g of picoline, and 50 g of DMF were added to the above solution and stirred at room temperature for an hour and at 120° C. for an hour. The solution was then poured into methanol for precipitation. The solid precipitate was ground and dried in a vacuum oven (90° C., 5 mmHg, for one night). Thus 12.5 g of polyimide composition (having a weight average molecular weight of 90,000) was obtained.

Example 8

4.75 g (10 mmol) of 12-(4-fluorocinnanic acid)-dodecane-1-(3,5-diaminobenzoate) prepared in Example 2 and 50 g of dimethylformamide (hereinafter referred to as "DMF") were placed in a 2000 mL separable flask equipped with a stirrer. Then 8.35 g (10 mmol) of acid dianhydride prepared in Example 1 was added at a dash with vigorous stirring, and continuously stirred for 30 minutes to obtain polyamic acid solution. 10 g of acetic anhydride, 5 g of β-picoline, and 50 g of DMF were added to the above solution and stirred at room temperature for an hour and at 120° C. for an hour. The solution was then poured into methanol for precipitation. The solid precipitate was ground and dried in a vacuum oven (90° C., 5 mmHg, for one night). Thus 12.3 g of polyimide composition (having a weight average molecular weight of 90,000) was obtained.

Example 9

4.42 g (10 mmol) of 12-(3,5-diaminobenzyloxy)-dodecane-1-(furylacrylate) prepared in Example 3 and 50 g of dimethylformamide (hereinafter referred to as "DMF") were placed in a 2000 mL separable flask equipped with a stirrer. Then 8.35 g (10 mmol) of the acid dianhydride prepared in Example 1 was added at a dash with vigorous stirring, and continuously stirred for 30 minutes to obtain polyamic acid solution. 10 g of acetic anhydride, 5 g of β-picoline, and 50 g of DMF were added to the above solution and stirred at room temperature for an hour and at 120° C. for an hour. The solution was poured into methanol for precipitation. The solid precipitate was then ground and dried in a vacuum oven (90° C., 5 mmHg, for one night). Thus 12.1 g of polyimide composition (having a weight average molecular weight of 75,000) was obtained.

Example 10

4.75 g (10 mmol) of 12-(4-fluorocinnamic acid)-dodecane-1-(3,5-diaminobenzoate) prepared in Example 2, 4.30 g (10 mmol) of bis[4-(3-aminophenoxy)phenyl]sulfone, and 100 g of dimethylformamide (hereinafter referred to as "DMF") were placed in a 2000 mL separable flask equipped with a stirrer. Then 8.35 g (10 mmol) of the acid dianhydride prepared in Example 1 was added at a dash with vigorous stirring, and continuously stirred for 30 minutes. Then, 5.76 g (10 mmol) of 2,2-bis(4-hydroxyphenyl)propanedibenzoate-3,3',4,4'-tetracarboxylic acid dianhydride was added at a dash and stirred for 30 minutes to obtain polyamic acid solution. 10 g of acetic anhydride, 5 g of β-picoline, and 50 g of DMF were added to the above solution and stirred at room temperature for an hour and at 120° C. for an hour. The solution was poured into methanol for precipitation. The solid precipitate was then ground and dried in a vacuum oven (90° C., 5 mmHg, for one night). Thus 21.3 g of polyimide composition (having a weight average molecular weight of 100,000) was obtained.

Example 11

7.35 g (10 mmol) of 1,1-{4,4'-bis[4-amino-2-(1hexadecane carboxylate)phenyl]}methane prepared in Example 4 and 50 g of dimethylformamide were placed in a 2000 mL separable flask equipped with a stirrer. Then 11.53 g (20 mmol) of ESDA was added at a dash with vigorous stirring, and continuously stirred for 30 minutes. Then, 2.86 g (10 mmol) of 3,5-diaminobenzyl-4-fluorocinnamate was added and stirred for 12 hours to obtain polyamic acid solution. A weight average molecular weight (hereinafter referred to as "Mw") of this polyamic acid was 38,000. In this case, the solution was subjected to reaction at room temperature under a nitrogen atmosphere.

10 g of acetic anhydride, 3 g of β-picoline, and 30 g of dimethylformamide were added to the above solution and stirred at room temperature for an hour and at 80° C. for an hour. The reaction solution was poured into methanol for precipitation. The solid precipitate was ground by a mixer, and then extracted using Soxhlet extractor (solvent: methanol) for 4 hours. The extracted residue was then dried, and thus 20.8 g of polyimide having a weight average molecular weight of 37,000 was obtained.

Example 12

7.91 g (10 mmol) of 1,1-{4,4'-bis[4-amino-3-(12-(4fluorocinnamic acid)-dodecane carboxylate)phenyl]}methane prepared in the aforementioned Example and 50 g of dimethylformamide were placed in a 2000 mL separable flask equipped with a stirrer. Then 11.53 g (20 mmol) of ESDA was added at a dash with vigorous stirring, and continuously stirred for 30 minutes. Then, 2.86 g (10 mol) of 3,5-diaminobenzyl-4-fluorocinnamate was added and stirred for 12 hours to obtain polyamic acid solution. A weight average molecular weight (hereinafter referred to as "Mw") of this polyamic acid was 51,000. In this case, the solution was subjected to reaction at room temperature under a nitrogen atmosphere.

10 g of acetic anhydride, 3 g of β-picoline, and 30 g of dimethylformamide were added to the above solution and stirred at room temperature for an hour and at 80° C. for an hour. The reaction solution was poured into methanol for precipitation. The solid precipitate was ground by a mixer, and then extracted using Soxhlet extractor (solvent: methanol) for 4 hours. The extracted residue was then dried, and thus 21.4 g of polyimide having a weight average molecular weight of 50,000 was obtained.

Example 13

0.5 wt % of bis-4,4'-diethylaminobenzophenone was added as a sensitizer to 100 wt % of the polyimide obtained in Example 7, and thus a polyimide composition of the present invention was obtained.

[Photosensitivity Test of Polyimide]

5 wt % of the polyimides and the polyimide compositions prepared in Examples 7 to 13 were dissolved in NMP, respectively. The respective solutions were then applied using a spin-coater to make a 1 μm-thick film, and dried at 80° C. for 30 minutes. A mask with a 50-μm-pitch line/space was placed on the film, and then light was applied thereto for 10 minutes using a high pressure mercury lamp (10 mW/cm$^2$). After that, the film was developed with a mixed solution of NPM and water. As the result, the film with a 50 μm pattern was obtained. This shows that photosensitivity was provided to the polyimides of the present invention.

INDUSTRIAL APPLICABILITY

As stated above, the present invention can provide a novel acid dianhydride and a novel diamine having a reactive group bonded through C2 to C30 alkylene group or C4 to C30 fluoroalkylene group. Further, the present invention can provide a novel diamine containing two alkyl groups having a carbon number of 6 to 30 and/or two fluoroalkyl groups having a carbon number of 4 to 30 in a molecular thereof and can provide a novel diamine having a reactive group at an end of the alkyl group and/or fluoroalkyl group. Particularly, the present invention can provide a novel polyimide containing the novel diamine and the novel acid dianhydride, which has both photoreactivity and thermoreactivity specific to the reactive group, and whose reactive group is selected from the group consisting of: organic groups derived from cinnamic acid, chalcone, furylacryloyl, benzalacetophenone, stilbene, coumarin, and pyrone; allyl, propargyl; ethinyl; $CH_2=CH-$; $CH_2=C(CH_3)-$ and skeletons derived therefrom, and can provide a novel polyimide composition containing such polyimide.

What is claimed is:

1. A polyimide composition comprising a polyimide prepared from:
an acid dianhydride; and
a diamine comprising a structure:

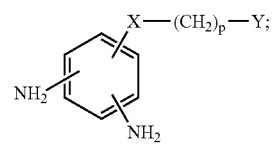

wherein X is selected from the group consisting of
—O—, —CH$_2$—O—and —COO—;

Y is a monovalent organic moiety having a first reactive group selected from the group consisting of propargyl, ethinyl, and a residue of cinnamic acid, chalcone, furylacryloyl, benzalacetophenone, stilbene, coumarin or pyrone;

p is an integer from 2 to 30; and the acid dianhydride comprises a second reactive group through a C2 to C30 alkylene group or a C4 to C30 fluoroalkylene group;

wherein the second reactive group is selected from the group consisting of allyl, propargyl, ethinyl, $CH_2$=CH—, $CH_2$=C($CH_3$)—, and a residue of cinnamic acid, chalcone, furylacryloyl, benzalacetophenone, stilbene, coumarin or pyrone.

2. The polyimide composition of claim 1 wherein the acid dianhydride comprises a structure:

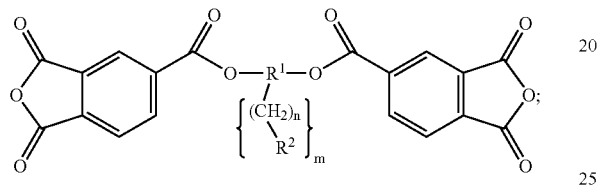

wherein $R^1$ comprises a trivalent or tetravalent organic group;

$R^2$ is selected from the group consisting of allyl, propargyl, ethinyl, $CH_2$=CH—, $CH_2$=C($CH_3$)—, and a residue of cinnamic acid, chalcone, furylacryloyl, benzalacetophenone, stilbene, coumarin or pyrone;

n is an integer from 2 to 30; and m is 1 or 2.

3. The polyimide composition of claim 1 wherein the acid dianhydride comprises a structure:

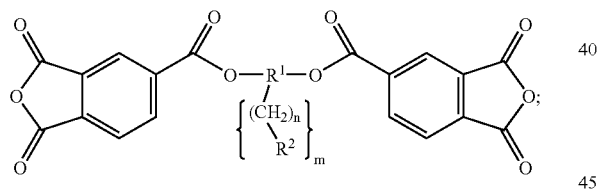

wherein n is an integer from 2 to 30;
m is 1 or 2;
$R^1$ is selected from the group consisting of:

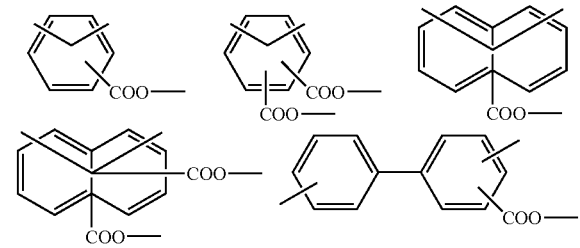

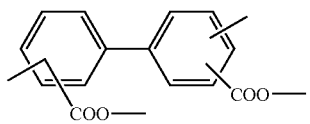

$R^2$ is selected from the group consistng of:

(II)

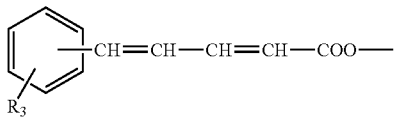

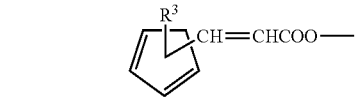

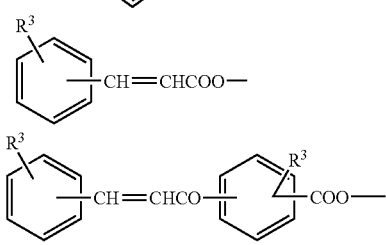

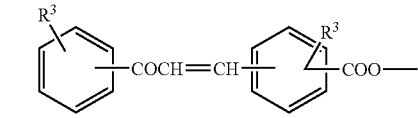

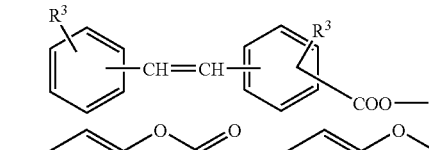

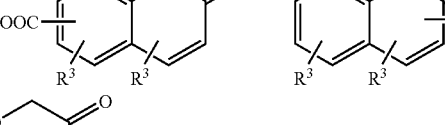

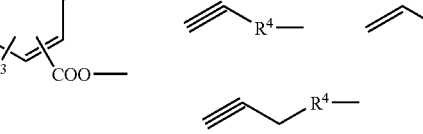

$R^3$ is selected from the group consistng of hydrogen, halogen, methoxy, an alkyl group having 1 to 20 carbon atoms; and $R^4$ is —O— or —COO—.

4. The polylmide composition as in any one of claims 1, 2 and 3, characterized by mixing 0.1 to 5.0 parts by weight of a sensitizer with 100 parts by weight of the polyimide.

* * * * *

UNITED STATES PATENT AND TRADEMARK OFFICE
CERTIFICATE OF CORRECTION

PATENT NO. : 7,396,898 B2  
APPLICATION NO. : 10/474855  
DATED : July 8, 2008  
INVENTOR(S) : Koji Okada Page 1 of 1

It is certified that error appears in the above-identified patent and that said Letters Patent is hereby corrected as shown below:

In the Claims

In column 40, Line 52, after the structure, in line 1, after "from the group" delete "consistng" and substitute --consisting-- in its place.

Signed and Sealed this

Twentieth Day of January, 2009

JON W. DUDAS  
*Director of the United States Patent and Trademark Office*

UNITED STATES PATENT AND TRADEMARK OFFICE
CERTIFICATE OF CORRECTION

PATENT NO. : 7,396,898 B2
APPLICATION NO. : 10/474855
DATED : July 8, 2008
INVENTOR(S) : Okada It is certified that error appears in the above-identified patent and that said Letters Patent is hereby corrected as shown below:

Title Page,

[*] Notice: Subject to any disclaimer, the term of this patent is extended or adjusted under 35 USC 154(b) by 427 days Delete the phrase "by 427 days" and insert -- by 413 days --

Signed and Sealed this

Twenty-eighth Day of July, 2009

JOHN DOLL
*Acting Director of the United States Patent and Trademark Office*